US011098349B2

(12) United States Patent
Driebe et al.

(10) Patent No.: US 11,098,349 B2
(45) Date of Patent: Aug. 24, 2021

(54) SYSTEMS AND METHODS OF DIAGNOSING AND CHARACTERIZING INFECTIONS

(71) Applicants: The Translational Genomics Research Institute, Phoenix, AZ (US); Arizona Board of Regents on Behalf of Northern Arizona University, Flagstaff, AZ (US)

(72) Inventors: Elizabeth Driebe, Flagstaff, AZ (US); Jolene Bowers, Flagstaff, AZ (US); David Engelthaler, Flagstaff, AZ (US); Paul Keim, Flagstaff, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 29 days.

(21) Appl. No.: 15/773,270

(22) PCT Filed: Nov. 3, 2016

(86) PCT No.: PCT/US2016/060369
§ 371 (c)(1),
(2) Date: May 3, 2018

(87) PCT Pub. No.: WO2017/079461
PCT Pub. Date: May 11, 2017

(65) Prior Publication Data
US 2019/0024139 A1    Jan. 24, 2019

Related U.S. Application Data

(60) Provisional application No. 62/250,565, filed on Nov. 4, 2015.

(51) Int. Cl.
*C12Q 1/686* (2018.01)
*C12Q 1/689* (2018.01)

(52) U.S. Cl.
CPC ............ *C12Q 1/686* (2013.01); *C12Q 1/689* (2013.01); *C12Q 2600/156* (2013.01); *C12Q 2600/16* (2013.01)

(58) Field of Classification Search
CPC ..... C12Q 1/686; C12Q 1/689; C12Q 2600/16
See application file for complete search history.

(56) References Cited

U.S. PATENT DOCUMENTS

| 7,695,941 | B2  |   | 4/2010  | Lin et al.   |              |
|-----------|-----|---|---------|--------------|--------------|
| 2005/0019893 | A1 |   | 1/2005  | Huletsky et al. |           |
| 2007/0082340 | A1 | * | 4/2007  | Huletsky     | C12Q 1/689   |
|           |     |   |         |              | 435/6.12     |
| 2010/0016276 | A1 | * | 1/2010  | Whiteford    | C12Q 1/689   |
|           |     |   |         |              | 514/210.04   |
| 2011/0312504 | A1 | * | 12/2011 | Driebe       | C12Q 1/689   |
|           |     |   |         |              | 506/2        |

FOREIGN PATENT DOCUMENTS

| WO | WO 2002034773 | * | 5/2002 | ............ C12Q 1/686 |
| WO | 2015/070187 A2 |   | 5/2015 | |

OTHER PUBLICATIONS

Colman, R.E. et al., Detection of Low-Level Mixed-Population Drug Resistance in *Mycobacterium tuberculosis* Using High Fidelity Amplicon Sequencing, PLOS ONE, vol. 10, e0126626, pp. 1-18 (Year: 2015).*
Diancourt, L. et al., Multilocus Sequence Typing of Klebsiella pneumoniae Nosocomial Isolates, J. Clin. Microbiol., vol. 43, pp. 4178-4182 (Year: 2005).*
Brisse, S. et al., Epidemiology of Quinolone Resistance of Klebsiella pneumoniae and Klebsiella oxytoca in Europe, Eur. J. Clin. Microbiol. Infect. Dis., vol. 19, pp. 64-68 (Year: 2000).*
Boers, S.A. et al., High-Throughput Multilocus Sequence Typing: Bringing Molecular Typing to the Next Level, PLOS ONE, vol. 7, e39630, pp. 1-8 (Year: 2012).*
Gen Bank Accession No. AY034847, Klebsiella pneumoniae carbapenemase (KPC-2) gene, complete cds (Year: 2003).*
Endimiani, A. et al., Characterization of blaKPC-containing Klebsiella pneumoniae isolates detected in different institutions in the Eastern USA, J. Antimicr. Chemother., vol. 63, pp. 427-437 (Year: 2009).*
Bratu, S. et al., Carbapenemase-producing Klebsiella pneumoniae in Brooklyn, NY: molecular epidemiology and in vitro activity of polymyxin B and other agents, J. Antimicr. Chemother., vol. 56, pp. 128-132 (Year: 2005).*
Brisse, S. et al., wzi Gene Sequencing, a Rapid Method for Determination of Capsular Type for Klebsiella Strains, J. Clin. Microbiol., vol. 51, pp. 4073-4078 (Year: 2013).*
Buck, G.A. et al., Design Strategies and Performance of Custom DNA Sequencing Primers, Biotechniques, vol. 27, pp. 528-536 (Year: 1999).*
GenBank Accession No. AB822494, *Klebsiella* sp. 1303/50 DNA, capsular polysaccharides biosynthesis gene cluster, partial sequence (Year: 2013).*
Martineau, F. et al., Development of a PCR Assay for Indetification of Staphylococci at Genus and Species Levels, J. Clin. Microbiol., vol. 30, pp. 2541-2547 (Year: 2001).*
GenBank Accession No. DQ414176, Staphylococcus aureus strain D456 TufA (tufA) gene, partial cds (Year: 2006).*
Hayden, M.J. et al., Multiplex-Ready PCR: A new method for multiplexed SSR and SNP genotyping, BMC Genomics, vol. 9:80, pp. 1-12, (Year: 2008).*
Jones, A.L. et al., Penicillin-binding proteins in Streptococcus agalactiae: a novel mechanism for evasion of immune clearance, Mol. Microbiol., vol. 47, pp. 247-256 (Year: 2003).*

(Continued)

*Primary Examiner* — Teresa E Strzelecka
(74) *Attorney, Agent, or Firm* — Rodney J. Fuller; Booth Udall Fuller, PLC

(57) ABSTRACT

Embodiments of the invention include methods of identifying microorganisms and/or diagnosing infections in subjects cause by microorganisms. Embodiments of the invention may also include further characterizing (e.g., determining the presence of one or more antibiotic resistance markers) the microorganisms and determining a strain identity of the microorganisms.

17 Claims, No Drawings
Specification includes a Sequence Listing.

(56) References Cited

OTHER PUBLICATIONS

Doi, Y., Klebsiella Pneumoniae Subsp. *pneumoniae* PittNDM01. Complete Genome. GenBank Accession CP006798.1. Submitted Sep. 30, 2013 [retrieved Mar. 15, 2017]. Retrieved from the Internet: <URL:https://www.ncbi.nlm.nih.gov/nucleotide/667708115?report=https://www.ncbi.nlm.nih.gov/nucleotide/667708115?report=genbank&log$=nuclalign&blast_rank=100&RID=CK5JPC1D016&from=2532663&to=2532681; pp. 1-2.

Dolman, Rebecca E et al., "Detection of Low-Level Mixed-Population Drug Resistance in *Mycobacterium tuberculosis* Using High Fidelity Amplicon Sequencing", PLOS ONE, 10(5):e0126626 (May 13, 2015).

Zhang, Kunyan et al., "New Quadriplex PCR Assay for Detection of Methicillin and Mupirocin Resistance and Simultaneous Discrimination of *Staphylococcus aureus*", Journal of Clinical Microbiology, 42(11):4947-4955 (Nov. 2004).

Strommenger, Birgit et al., "Multiplex PCR Assay for Simultaneous Detection of Nine Clinically Relevant Antibiotic Resistance Genes in *Staphylococcus aureus*", Journal of Clinical Microbiology, 41(9):4089-4094 (Sep. 2003).

Ho, Jack Y. et al., "Rapid Identification of ESKAPE Bacterial Strains Using an Autonomous Microfluidic Device", PLOS ONE, 7(7):e41245 (Jul. 27, 2012).

Perez-Roth, E. et al., "Multiplex PCR for Simultaneous Identification of *Staphylococcus aureus* and Detection of Methicillin and Mupirocin Resistance", Journal of Clinical Microbiology, 39(11):4037-4041 (Nov. 2001).

\* cited by examiner

SEQUENCE LISTING

<160> NUMBER OF SEQ ID NOS: 431

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
cgtttcacaa ctgcggatg                                              19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tggcggtcat gttcttactc                                             20

<210> SEQ ID NO 3
<211> LENGTH: 17
<212> TYPE: DNA
<213> ORGANISM: Artificial Sequence

```
<220> FEATURE:
<223> OTHER INFORMATION: Primer

<400> SEQUENCE: 3
ttcacaccgc catcgtc                                              17

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
cagcatctcc accgacag                                             18

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
cgttcctcac cgtagtgg                                             18

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
tccagcgtga cataatcgg                                            19

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tttccaccta cgccgataaa g                                         21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ccagcggaat aaccaggac                                            19

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
ggcggcgatg agtttgt                                              17
```

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
atgttgcgga tagcctgata g                                              21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cgctccacta tcaggctatc                                                20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ttcggcgatg ggaataaaca                                                20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tgcctatcgc cactttattg a                                              21

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cggtcgttaa tcgcccttct                                                19

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
cctcaggtac gctcattcg                                                 19

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
tcgtcacatc cctcctctt                                              19

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gatcagcagc aaacggtgac                                             20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggcgatgtaa tcctgcgaga                                             20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gggatatccg tggaatgcgt                                             20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
taatgtgatc accgctcccg                                             20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
acgagccagc ctgatgaaaa                                             20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
catcgcaact gctgcatctc                                             20

```
<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gccttgcgcc ttagtttgtt                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggctatccat tttccagccg                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ttcttttcca ggagcaacgc                                              20

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
agcaagacag aaataagtaa aaaga                                        25

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tcttcgtcat ggtgsgtttc                                              20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aacggaacat ggtgagcaac                                              20

<210> SEQ ID NO 29
<211> LENGTH: 20
<212> TYPE: DNA
<213> ORGANISM: Artificial Sequence
<220> FEATURE:
<223> OTHER INFORMATION: Primer
```

```
<400> SEQUENCE: 29
gktttgatgg ctgggtcagt                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgtttggctt tttgcagttg                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tacttrgctt tttgcagttg                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcagtgaaaa cracccacga                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
atygctgctg tccgagttct                                               20

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
ccgtcgccgt attactgat                                                19

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tctctacaac acgctaccct a                                             21
```

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ggtgagaacg atgtgattgt g                                              21

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
tgacccaaag gcgattcg                                                  18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
gaagcggttg aggaacag                                                  18

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
acccacgaca tgatgtac                                                  18

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ggacgatcca ttccataccg                                                20

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
gacgaagcgg tgatccac                                                  18

<210> SEQ ID NO 42
<211> LENGTH: 21
<212> TYPE: DNA
<213> ORGANISM: Artificial Sequence
<220> FEATURE:
<223> OTHER INFORMATION: Primer

```
<400> SEQUENCE: 42
ataggtgtgg cttttgtagg g                                          21

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
ctgctgctaa taacgcttgc                                            20

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
atggttatga aattgttggt gatgaa                                     26

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
ccgttgcttg atattctttc gtat                                       24

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tacgaaatca gaagtggctc aa                                         22

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
acgttaaatc ctgcattttc caa                                        23

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
tagcgttggt attaagtggt tgt                                        23
```

```
<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
gtcatagcat agttcgggtc a                                              21

<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50
acwggccgtg ttgaacgtg                                                 19

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
caccagcttc agcgtagtct aat                                            23

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
ctcaacwggc atcatgaatg gttt                                           24

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
aggtgacgat gtrcctgtaa tc                                             22

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
cgttgtttgc gaccygtata                                                20

<210> SEQ ID NO 55
<211> LENGTH: 22
<212> TYPE: DNA
<213> ORGANISM: Artificial Sequence
<220> FEATURE:
<223> OTHER INFORMATION: Primer
```

```
<400> SEQUENCE: 55
aatgtaaatt cgctgrgatc gt                                              22

<210> SEQ ID NO 56
<211> LENGTH: 17
<212> TYPE: DNA
<213> ORGANISM: Artificial Sequence
<220> FEATURE:
<223> OTHER INFORMATION: Primer

<400> SEQUENCE: 56
cgcctggctc tgtttca                                                    17

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
agcaagtgca ttacgagtct                                                 20

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
gtctgttgaa tgatgatgta tgtcg                                           25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
atcccatttt acaaatggca aaaca                                           25

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
tgcagaacta gcccatttta ca                                              22

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
tgcwgaacta kcccatttta ca                                              22
```

```
<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
tttagcgrac agatttggtt taca                                          24

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
cggttgcctt gctgagtt                                                 18

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
tccgyaaacc tcaactcatt t                                             21

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
gccagtgaac catctaatac agt                                           23

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
tagagcagca acaaatcaac aaga                                          24

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
ttattatgag tcgccttggc aatt                                          24

<210> SEQ ID NO 68
<211> LENGTH: 24
<212> TYPE: DNA
<213> ORGANISM: Artificial Sequence
<220> FEATURE:
<223> OTHER INFORMATION: Primer
```

```
<400> SEQUENCE: 68
tagagcagca acaaatcaac aaga                                              24

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
tcgcatggct tctgactca                                                    19

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
aaattgcyaa agcacaaggt tt                                                22

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
cgggaattgc ytcatggtaa g                                                 21

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
gatagcgatt actcggttcc atc                                               23

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
cctgtgccta aaaccagtga aa                                                22

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
tcctgatata atcggtgtca caag                                              24
```

```
<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
agaacaagag gtatgtcatc taactt                                          26

<210> SEQ ID NO 76
<211> LENGTH: 26
<212> TYPE: DNA
<213> ORGANISM: Artificial Sequence
<220> FEATURE:
<223> OTHER INFORMATION: Primer

<400> SEQUENCE: 76
ctgatggata tggagacatt aaggat                                          26

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
gtccaattat atgcggatct atacct                                          26

<210> SEQ ID NO 78
<211> LENGTH: 26
<212> TYPE: DNA
<213> ORGANISM: Artificial Sequence
<220> FEATURE:
<223> OTHER INFORMATION: Primer

<400> SEQUENCE: 78
ctgatggata tggagacatt aaggat                                          26

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
aattagttga gtagccatga cagt                                            24

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
tacggtgtaa gtgctgataa agg                                             23

<210> SEQ ID NO 81
<211> LENGTH: 25
<212> TYPE: DNA
<213> ORGANISM: Artificial Sequence
<220> FEATURE:
<223> OTHER INFORMATION: Primer
```

<400> SEQUENCE: 81
gcttcaaagt taagtccatc caaat                                        25

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
gccaaccgtg gtatgtca                                                18

<210> SEQ ID NO 83
<211> LENGTH: 18
<212> TYPE: DNA
<213> ORGANISM: Artificial Sequence
<220> FEATURE:
<223> OTHER INFORMATION: Primer

<400> SEQUENCE: 83
ttctgccggg tttctttg                                                18

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
ctcgtgctgc tacttctc                                                18

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
cgtggatgtg ctygttaaca ac                                           22

<210> SEQ ID NO 86
<211> LENGTH: 19
<212> TYPE: DNA
<213> ORGANISM: Artificial Sequence
<220> FEATURE:
<223> OTHER INFORMATION: Primer

<400> SEQUENCE: 86
aacttrtcct tgtgcttgc                                               19

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
acatagtcgt tggcatacag a                                            21

```
<210> SEQ ID NO 88
<211> LENGTH: 23
<212> TYPE: DNA
<213> ORGANISM: Artificial Sequence
<220> FEATURE:
<223> OTHER INFORMATION: Primer

<400> SEQUENCE: 88
attgttgatg actgttcctc ttc                                            23

<210> SEQ ID NO 89
<211> LENGTH: 18
<212> TYPE: DNA
<213> ORGANISM: Artificial Sequence
<220> FEATURE:
<223> OTHER INFORMATION: Primer

<400> SEQUENCE: 89
cgacgaygat gacgaatg                                                  18

<210> SEQ ID NO 90
<211> LENGTH: 19
<212> TYPE: DNA
<213> ORGANISM: Artificial Sequence
<220> FEATURE:
<223> OTHER INFORMATION: Primer

<400> SEQUENCE: 90
cgcaattaag tcggtcctg                                                 19

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
ccttcaacgt gratgttcag                                                20

<210> SEQ ID NO 92
<211> LENGTH: 19
<212> TYPE: DNA
<213> ORGANISM: Artificial Sequence
<220> FEATURE:
<223> OTHER INFORMATION: Primer

<400> SEQUENCE: 92
aatwccyact tcgccttca                                                 19

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
tggcgttctg gaygtcaa                                                  18

<210> SEQ ID NO 94
<211> LENGTH: 21
<212> TYPE: DNA
<213> ORGANISM: Artificial Sequence
<220> FEATURE:
<223> OTHER INFORMATION: Primer
```

<400> SEQUENCE: 94
agttgtttat accgccaaag c					21

<210> SEQ ID NO 95
<211> LENGTH: 21
<212> TYPE: DNA
<213> ORGANISM: Artificial Sequence
<220> FEATURE:
<223> OTHER INFORMATION: Primer

<400> SEQUENCE: 95
agttgtctac actgccaaag c					21

<210> SEQ ID NO 96
<211> LENGTH: 25
<212> TYPE: DNA
<213> ORGANISM: Artificial Sequence
<220> FEATURE:
<223> OTHER INFORMATION: Primer

<400> SEQUENCE: 96
acccaaaagt attctgattg ttgag				25

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
atgaggtctt attatcggtc aactg				25

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
aatcggcaat accagcagtt					20

<210> SEQ ID NO 99
<211> LENGTH: 25
<212> TYPE: DNA
<213> ORGANISM: Artificial Sequence
<220> FEATURE:
<223> OTHER INFORMATION: Primer

<400> SEQUENCE: 99
ccttcacgga ataacatatc cagat				25

<210> SEQ ID NO 100
<211> LENGTH: 25
<212> TYPE: DNA
<213> ORGANISM: Artificial Sequence
<220> FEATURE:
<223> OTHER INFORMATION: Primer

<400> SEQUENCE: 100
gcttattgct aatgactgtg cttat				25

```
<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
tgccgacatt gacaaccata                                              20

<210> SEQ ID NO 102
<211> LENGTH: 23
<212> TYPE: DNA
<213> ORGANISM: Artificial Sequence
<220> FEATURE:
<223> OTHER INFORMATION: Primer

<400> SEQUENCE: 102
catctgcttg acctttatga aac                                          23

<210> SEQ ID NO 103
<211> LENGTH: 23
<212> TYPE: DNA
<213> ORGANISM: Artificial Sequence
<220> FEATURE:
<223> OTHER INFORMATION: Primer

<400> SEQUENCE: 103
gtgaggctaa cacatcaaac tag                                          23

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
atgcgggagg tctgtttcta c                                            21

<210> SEQ ID NO 105
<211> LENGTH: 19
<212> TYPE: DNA
<213> ORGANISM: Artificial Sequence
<220> FEATURE:
<223> OTHER INFORMATION: Primer

<400> SEQUENCE: 105
ccagccggta aagaaactc                                               19

<210> SEQ ID NO 106
<211> LENGTH: 24
<212> TYPE: DNA
<213> ORGANISM: Artificial Sequence
<220> FEATURE:
<223> OTHER INFORMATION: Primer

<400> SEQUENCE: 106
gtcaagcacc ttaycaccat ctag                                         24

<210> SEQ ID NO 107
<211> LENGTH: 19
<212> TYPE: DNA
<213> ORGANISM: Artificial Sequence
<220> FEATURE:
<223> OTHER INFORMATION: Primer
```

<400> SEQUENCE: 107
ggcatgcttg tgaacaaca                                                    19

<210> SEQ ID NO 108
<211> LENGTH: 23
<212> TYPE: DNA
<213> ORGANISM: Artificial Sequence
<220> FEATURE:
<223> OTHER INFORMATION: Primer

<400> SEQUENCE: 108
gtgccrattg aggatctggt ttc                                               23

<210> SEQ ID NO 109
<211> LENGTH: 22
<212> TYPE: DNA
<213> ORGANISM: Artificial Sequence
<220> FEATURE:
<223> OTHER INFORMATION: Primer

<400> SEQUENCE: 109
cygttggacc acttcctgtc at                                                22

<210> SEQ ID NO 110
<211> LENGTH: 21
<212> TYPE: DNA
<213> ORGANISM: Artificial Sequence
<220> FEATURE:
<223> OTHER INFORMATION: Primer

<400> SEQUENCE: 110
cgtctagttc tgctgtcttg t                                                 21

<210> SEQ ID NO 111
<211> LENGTH: 18
<212> TYPE: DNA
<213> ORGANISM: Artificial Sequence
<220> FEATURE:
<223> OTHER INFORMATION: Primer

<400> SEQUENCE: 111
accgtcatgc ctgttgtc                                                     18

<210> SEQ ID NO 112
<211> LENGTH: 23
<212> TYPE: DNA
<213> ORGANISM: Artificial Sequence
<220> FEATURE:
<223> OTHER INFORMATION: Primer

<400> SEQUENCE: 112
ttgttgattg gctaaaggga aac                                               23

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
cagacgacgg catagtcatt                                                   20

```
<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
ggacaagatg ggcggtatg                                                  19

<210> SEQ ID NO 115
<211> LENGTH: 17
<212> TYPE: DNA
<213> ORGANISM: Artificial Sequence
<220> FEATURE:
<223> OTHER INFORMATION: Primer

<400> SEQUENCE: 115
cggcgtagtg ctcagtg                                                    17

<210> SEQ ID NO 116
<211> LENGTH: 21
<212> TYPE: DNA
<213> ORGANISM: Artificial Sequence
<220> FEATURE:
<223> OTHER INFORMATION: Primer

<400> SEQUENCE: 116
caactggatc aagcaggaga t                                               21

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
cgacaacgca ttggcataag                                                 20

<210> SEQ ID NO 118
<211> LENGTH: 22
<212> TYPE: DNA
<213> ORGANISM: Artificial Sequence
<220> FEATURE:
<223> OTHER INFORMATION: Primer

<400> SEQUENCE: 118
gaattggact gcctctacga tt                                              22

<210> SEQ ID NO 119
<211> LENGTH: 18
<212> TYPE: DNA
<213> ORGANISM: Artificial Sequence
<220> FEATURE:
<223> OTHER INFORMATION: Primer

<400> SEQUENCE: 119
gcacgcccat acagatgt                                                   18

<210> SEQ ID NO 120
<211> LENGTH: 17
<212> TYPE: DNA
<213> ORGANISM: Artificial Sequence
<220> FEATURE:
<223> OTHER INFORMATION: Primer
```

```
<400> SEQUENCE: 120
aaggcatgga ggcgaac                                                17

<210> SEQ ID NO 121
<211> LENGTH: 26
<212> TYPE: DNA
<213> ORGANISM: Artificial Sequence
<220> FEATURE:
<223> OTHER INFORMATION: Primer

<400> SEQUENCE: 121
aagtatataa gttctgttcc gatggt                                      26

<210> SEQ ID NO 122
<211> LENGTH: 24
<212> TYPE: DNA
<213> ORGANISM: Artificial Sequence
<220> FEATURE:
<223> OTHER INFORMATION: Primer

<400> SEQUENCE: 122
aatactccac actttatcca ccaa                                        24

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
ttcttgcgaa cctccttctc                                             20

<210> SEQ ID NO 124
<211> LENGTH: 19
<212> TYPE: DNA
<213> ORGANISM: Artificial Sequence
<220> FEATURE:
<223> OTHER INFORMATION: Primer

<400> SEQUENCE: 124
aacgatgcga cgatccatt                                              19

<210> SEQ ID NO 125
<211> LENGTH: 18
<212> TYPE: DNA
<213> ORGANISM: Artificial Sequence
<220> FEATURE:
<223> OTHER INFORMATION: Primer

<400> SEQUENCE: 125
gcgatttgct gtgcgaaa                                               18

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
ccgcttgctg gtacatatct a                                           21
```

```
<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
cctatctcgt ccgctatctg                                            20

<210> SEQ ID NO 128
<211> LENGTH: 24
<212> TYPE: DNA
<213> ORGANISM: Artificial Sequence
<220> FEATURE:
<223> OTHER INFORMATION: Primer

<400> SEQUENCE: 128
actattctgc ctatcctaat tggg                                       24

<210> SEQ ID NO 129
<211> LENGTH: 24
<212> TYPE: DNA
<213> ORGANISM: Artificial Sequence
<220> FEATURE:
<223> OTHER INFORMATION: Primer

<400> SEQUENCE: 129
tcatttaatg ttgcgactct ttca                                       24

<210> SEQ ID NO 130
<211> LENGTH: 28
<212> TYPE: DNA
<213> ORGANISM: Artificial Sequence
<220> FEATURE:
<223> OTHER INFORMATION: Primer

<400> SEQUENCE: 130
atgactataa caaagcytac aagaaatc                                   28

<210> SEQ ID NO 131
<211> LENGTH: 26
<212> TYPE: DNA
<213> ORGANISM: Artificial Sequence
<220> FEATURE:
<223> OTHER INFORMATION: Primer

<400> SEQUENCE: 131
acaatggttt cataaacagc taagtc                                     26

<210> SEQ ID NO 132
<211> LENGTH: 21
<212> TYPE: DNA
<213> ORGANISM: Artificial Sequence
<220> FEATURE:
<223> OTHER INFORMATION: Primer

<400> SEQUENCE: 132
aacaagccct acaagaaatc c                                          21

<210> SEQ ID NO 133
<211> LENGTH: 17
<212> TYPE: DNA
<213> ORGANISM: Artificial Sequence
<220> FEATURE:
<223> OTHER INFORMATION: Primer
```

<400> SEQUENCE: 133
cgcacttcgg tgtatcg                                                      17

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
aacaagccct acaagaaatc c                                                 21

<210> SEQ ID NO 135
<211> LENGTH: 17
<212> TYPE: DNA
<213> ORGANISM: Artificial Sequence
<220> FEATURE:
<223> OTHER INFORMATION: Primer

<400> SEQUENCE: 135
ctcggtgcca tcgtagt                                                      17

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
cattgccaga tgttcgtgac                                                   20

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
gccatcaaca agcggataac                                                   20

<210> SEQ ID NO 138
<211> LENGTH: 18
<212> TYPE: DNA
<213> ORGANISM: Artificial Sequence
<220> FEATURE:
<223> OTHER INFORMATION: Primer

<400> SEQUENCE: 138
aaatctgccc gtgtcgtt                                                     18

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
accatccacc agcatgtaac                                                   20

<210> SEQ ID NO 140
<211> LENGTH: 23
<212> TYPE: DNA
<213> ORGANISM: Artificial Sequence
<220> FEATURE:
<223> OTHER INFORMATION: Primer

<400> SEQUENCE: 140
ctcctatctg gattatgcga tgt                                    23

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
cgtcaataga accgaagtta cc                                     22

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
caatgactgg aacaaagcct                                        20

<210> SEQ ID NO 143
<211> LENGTH: 20
<212> TYPE: DNA
<213> ORGANISM: Artificial Sequence
<220> FEATURE:
<223> OTHER INFORMATION: Primer

<400> SEQUENCE: 143
cgatggaacc aaagttaccc                                        20

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
ttgtagtgtt ccaggtcgtc                                        20

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
ccgtctgcta ttgttcaagg                                        20

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
gaaattcaaa aagtccgccc					20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
ggatagcggt aagagaacgg					20

<210> SEQ ID NO 148
<211> LENGTH: 20
<212> TYPE: DNA
<213> ORGANISM: Artificial Sequence
<220> FEATURE:
<223> OTHER INFORMATION: Primer

<400> SEQUENCE: 148
cagcgcgaaa ttcaaaaagt					20

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
gcgaaagatt tgggatcgtc					20

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
gttctcttac cgttatccgc					20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
tatttcgaca accgggattc					20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
tgtgtatgcg atgtctgaac					20

```
<210> SEQ ID NO 153
<211> LENGTH: 21
<212> TYPE: DNA
<213> ORGANISM: Artificial Sequence
<220> FEATURE:
<223> OTHER INFORMATION: Primer

<400> SEQUENCE: 153
atatttcgac aaccgggatt c                                              21

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
gagcgagcta ggcttaaaaa                                                20

<210> SEQ ID NO 155
<211> LENGTH: 20
<212> TYPE: DNA
<213> ORGANISM: Artificial Sequence
<220> FEATURE:
<223> OTHER INFORMATION: Primer

<400> SEQUENCE: 155
tcccctgacc ttcgattaaa                                                20

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
gtacgtcatt atggaccgtg                                                20

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
ctataagccg agagtttggc                                                20

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
tccgtaaaag tgcgaaaaca                                                20

<210> SEQ ID NO 159
<211> LENGTH: 20
<212> TYPE: DNA
<213> ORGANISM: Artificial Sequence
<220> FEATURE:
<223> OTHER INFORMATION: Primer
```

<400> SEQUENCE: 159
agcttcagtg taacgcattg                                              20

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
ccagatgttc gtgatggttt                                              20

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
cttagcttca gtgtaacgca                                              20

<210> SEQ ID NO 162
<211> LENGTH: 20
<212> TYPE: DNA
<213> ORGANISM: Artificial Sequence
<220> FEATURE:
<223> OTHER INFORMATION: Primer

<400> SEQUENCE: 162
tagagttcag ggagtgcgat                                              20

<210> SEQ ID NO 163
<211> LENGTH: 23
<212> TYPE: DNA
<213> ORGANISM: Artificial Sequence
<220> FEATURE:
<223> OTHER INFORMATION: Primer

<400> SEQUENCE: 163
ccgagcagaa gtacatctta tgg                                          23

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
gatttgagyg acagccgttt                                              20

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165
gcagaagtac atcttatggc tga                                          23

<210> SEQ ID NO 166
<211> LENGTH: 24
<212> TYPE: DNA
<213> ORGANISM: Artificial Sequence
<220> FEATURE:
<223> OTHER INFORMATION: Primer

<400> SEQUENCE: 166
gctaatttct cacaggcaaa cttt                                    24

<210> SEQ ID NO 167
<211> LENGTH: 22
<212> TYPE: DNA
<213> ORGANISM: Artificial Sequence
<220> FEATURE:
<223> OTHER INFORMATION: Primer

<400> SEQUENCE: 167
acaacccgta atgtaagcag ag                                      22

<210> SEQ ID NO 168
<211> LENGTH: 23
<212> TYPE: DNA
<213> ORGANISM: Artificial Sequence
<220> FEATURE:
<223> OTHER INFORMATION: Primer

<400> SEQUENCE: 168
gtttgattgg tctttggctg att                                     23

<210> SEQ ID NO 169
<211> LENGTH: 21
<212> TYPE: DNA
<213> ORGANISM: Artificial Sequence
<220> FEATURE:
<223> OTHER INFORMATION: Primer

<400> SEQUENCE: 169
ccatccaact tcactccatc t                                       21

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
cgacaggaat agcttggaag g                                       21

<210> SEQ ID NO 171
<211> LENGTH: 21
<212> TYPE: DNA
<213> ORGANISM: Artificial Sequence
<220> FEATURE:
<223> OTHER INFORMATION: Primer

<400> SEQUENCE: 171
ccagttatca cagtgccatt c                                       21

<210> SEQ ID NO 172
<211> LENGTH: 20
<212> TYPE: DNA
<213> ORGANISM: Artificial Sequence
<220> FEATURE:
<223> OTHER INFORMATION: Primer

<400> SEQUENCE: 172
caatttatgc cacgccgaac                                              20

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
taatttatgt cacgccgaac                                              20

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
gataaacaac aatacccagt gctt                                         24

<210> SEQ ID NO 175
<211> LENGTH: 21
<212> TYPE: DNA
<213> ORGANISM: Artificial Sequence
<220> FEATURE:
<223> OTHER INFORMATION: Primer

<400> SEQUENCE: 175
gtgctaactt gcgtgatacg a                                            21

<210> SEQ ID NO 176
<211> LENGTH: 26
<212> TYPE: DNA
<213> ORGANISM: Artificial Sequence
<220> FEATURE:
<223> OTHER INFORMATION: Primer

<400> SEQUENCE: 176
tccatattgg cataggaaag attaca                                       26

<210> SEQ ID NO 177
<211> LENGTH: 26
<212> TYPE: DNA
<213> ORGANISM: Artificial Sequence
<220> FEATURE:
<223> OTHER INFORMATION: Primer

<400> SEQUENCE: 177
tccatattgg cataagacag gttaca                                       26

<210> SEQ ID NO 178
<211> LENGTH: 21
<212> TYPE: DNA
<213> ORGANISM: Artificial Sequence
<220> FEATURE:
<223> OTHER INFORMATION: Primer

<400> SEQUENCE: 178
gacgttcagt ggttcrgatc t                                            21

```
<210> SEQ ID NO 179
<211> LENGTH: 18
<212> TYPE: DNA
<213> ORGANISM: Artificial Sequence
<220> FEATURE:
<223> OTHER INFORMATION: Primer

<400> SEQUENCE: 179
kgctcgccag tcgaaagt                                                 18

<210> SEQ ID NO 180
<211> LENGTH: 22
<212> TYPE: DNA
<213> ORGANISM: Artificial Sequence
<220> FEATURE:
<223> OTHER INFORMATION: Primer

<400> SEQUENCE: 180
cgacgttcag tggttcrgat ct                                            22

<210> SEQ ID NO 181
<211> LENGTH: 18
<212> TYPE: DNA
<213> ORGANISM: Artificial Sequence
<220> FEATURE:
<223> OTHER INFORMATION: Primer

<400> SEQUENCE: 181
gckgctcgcc agtcgaaa                                                 18

<210> SEQ ID NO 182
<211> LENGTH: 23
<212> TYPE: DNA
<213> ORGANISM: Artificial Sequence
<220> FEATURE:
<223> OTHER INFORMATION: Primer

<400> SEQUENCE: 182
accaatctaa gctacgccaa ctt                                           23

<210> SEQ ID NO 183
<211> LENGTH: 19
<212> TYPE: DNA
<213> ORGANISM: Artificial Sequence
<220> FEATURE:
<223> OTHER INFORMATION: Primer

<400> SEQUENCE: 183
cctgagttcc catccagcg                                                19

<210> SEQ ID NO 184
<211> LENGTH: 22
<212> TYPE: DNA
<213> ORGANISM: Artificial Sequence
<220> FEATURE:
<223> OTHER INFORMATION: Primer

<400> SEQUENCE: 184
tacgcactgt gatttgacca at                                            22

<210> SEQ ID NO 185
<211> LENGTH: 20
<212> TYPE: DNA
<213> ORGANISM: Artificial Sequence
<220> FEATURE:
<223> OTHER INFORMATION: Primer
```

```
<400> SEQUENCE: 185
ggakcaacga tgcctggtag                                              20

<210> SEQ ID NO 186
<211> LENGTH: 24
<212> TYPE: DNA
<213> ORGANISM: Artificial Sequence
<220> FEATURE:
<223> OTHER INFORMATION: Primer

<400> SEQUENCE: 186
cgcatatatc accaatacca actt                                         24

<210> SEQ ID NO 187
<211> LENGTH: 20
<212> TYPE: DNA
<213> ORGANISM: Artificial Sequence
<220> FEATURE:
<223> OTHER INFORMATION: Primer

<400> SEQUENCE: 187
gttccaggak caacgatgcc                                              20

<210> SEQ ID NO 188
<211> LENGTH: 19
<212> TYPE: DNA
<213> ORGANISM: Artificial Sequence
<220> FEATURE:
<223> OTHER INFORMATION: Primer

<400> SEQUENCE: 188
ccgtcacgct gttgttagg                                               19

<210> SEQ ID NO 189
<211> LENGTH: 21
<212> TYPE: DNA
<213> ORGANISM: Artificial Sequence
<220> FEATURE:
<223> OTHER INFORMATION: Primer

<400> SEQUENCE: 189
cgctcatcag cacgataaag t                                            21

<210> SEQ ID NO 190
<211> LENGTH: 23
<212> TYPE: DNA
<213> ORGANISM: Artificial Sequence
<220> FEATURE:
<223> OTHER INFORMATION: Primer

<400> SEQUENCE: 190
cgctgattct ggtcatttac ttc                                          23

<210> SEQ ID NO 191
<211> LENGTH: 19
<212> TYPE: DNA
<213> ORGANISM: Artificial Sequence
<220> FEATURE:
<223> OTHER INFORMATION: Primer

<400> SEQUENCE: 191
acggctttct gccttaggt                                               19
```

```
<210> SEQ ID NO 192
<211> LENGTH: 19
<212> TYPE: DNA
<213> ORGANISM: Artificial Sequence
<220> FEATURE:
<223> OTHER INFORMATION: Primer

<400> SEQUENCE: 192
cgatgtgcag caccagtaa                                                  19

<210> SEQ ID NO 193
<211> LENGTH: 21
<212> TYPE: DNA
<213> ORGANISM: Artificial Sequence
<220> FEATURE:
<223> OTHER INFORMATION: Primer

<400> SEQUENCE: 193
tcggttcgct ttcactttc t                                                21

<210> SEQ ID NO 194
<211> LENGTH: 19
<212> TYPE: DNA
<213> ORGANISM: Artificial Sequence
<220> FEATURE:
<223> OTHER INFORMATION: Primer

<400> SEQUENCE: 194
gacgatgtca ctggctgag                                                  19

<210> SEQ ID NO 195
<211> LENGTH: 18
<212> TYPE: DNA
<213> ORGANISM: Artificial Sequence
<220> FEATURE:
<223> OTHER INFORMATION: Primer

<400> SEQUENCE: 195
ccacaaccca ggaagcag                                                   18

<210> SEQ ID NO 196
<211> LENGTH: 18
<212> TYPE: DNA
<213> ORGANISM: Artificial Sequence
<220> FEATURE:
<223> OTHER INFORMATION: Primer

<400> SEQUENCE: 196
tggcgcagac cctgaaaa                                                   18

<210> SEQ ID NO 197
<211> LENGTH: 21
<212> TYPE: DNA
<213> ORGANISM: Artificial Sequence
<220> FEATURE:
<223> OTHER INFORMATION: Primer

<400> SEQUENCE: 197
atatcgttgg tggtgccata a                                               21

<210> SEQ ID NO 198
<211> LENGTH: 18
<212> TYPE: DNA
<213> ORGANISM: Artificial Sequence
<220> FEATURE:
<223> OTHER INFORMATION: Primer
```

<400> SEQUENCE: 198
atggcgcaga ccctgaaa                                                    18

<210> SEQ ID NO 199
<211> LENGTH: 18
<212> TYPE: DNA
<213> ORGANISM: Artificial Sequence
<220> FEATURE:
<223> OTHER INFORMATION: Primer

<400> SEQUENCE: 199
ccgctgccgg ttttatcg                                                    18

<210> SEQ ID NO 200
<211> LENGTH: 18
<212> TYPE: DNA
<213> ORGANISM: Artificial Sequence
<220> FEATURE:
<223> OTHER INFORMATION: Primer

<400> SEQUENCE: 200
gagccgacgc tcaacacc                                                    18

<210> SEQ ID NO 201
<211> LENGTH: 18
<212> TYPE: DNA
<213> ORGANISM: Artificial Sequence
<220> FEATURE:
<223> OTHER INFORMATION: Primer

<400> SEQUENCE: 201
cccgacaacc cacgatgt                                                    18

<210> SEQ ID NO 202
<211> LENGTH: 18
<212> TYPE: DNA
<213> ORGANISM: Artificial Sequence
<220> FEATURE:
<223> OTHER INFORMATION: Primer

<400> SEQUENCE: 202
gctcaacacc gcgatccc                                                    18

<210> SEQ ID NO 203
<211> LENGTH: 18
<212> TYPE: DNA
<213> ORGANISM: Artificial Sequence
<220> FEATURE:
<223> OTHER INFORMATION: Primer

<400> SEQUENCE: 203
cccgacaacc cacgatgt                                                    18

<210> SEQ ID NO 204
<211> LENGTH: 19
<212> TYPE: DNA
<213> ORGANISM: Artificial Sequence
<220> FEATURE:
<223> OTHER INFORMATION: Primer

<400> SEQUENCE: 204
ttcgtctgga tcgcactga                                                   19

```
<210> SEQ ID NO 205
<211> LENGTH: 20
<212> TYPE: DNA
<213> ORGANISM: Artificial Sequence
<220> FEATURE:
<223> OTHER INFORMATION: Primer

<400> SEQUENCE: 205
gatgattctc gccgctgaag                                              20

<210> SEQ ID NO 206
<211> LENGTH: 19
<212> TYPE: DNA
<213> ORGANISM: Artificial Sequence
<220> FEATURE:
<223> OTHER INFORMATION: Primer

<400> SEQUENCE: 206
cgctggttct ggtgaccta                                               19

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
gatgattctc gccgctgaag                                              20

<210> SEQ ID NO 208
<211> LENGTH: 19
<212> TYPE: DNA
<213> ORGANISM: Artificial Sequence
<220> FEATURE:
<223> OTHER INFORMATION: Primer

<400> SEQUENCE: 208
aatggctgtt ggttggacg                                               19

<210> SEQ ID NO 209
<211> LENGTH: 23
<212> TYPE: DNA
<213> ORGANISM: Artificial Sequence
<220> FEATURE:
<223> OTHER INFORMATION: Primer

<400> SEQUENCE: 209
catactttcg gttgggtaat gct                                          23

<210> SEQ ID NO 210
<211> LENGTH: 23
<212> TYPE: DNA
<213> ORGANISM: Artificial Sequence
<220> FEATURE:
<223> OTHER INFORMATION: Primer

<400> SEQUENCE: 210
aatatgccgt tgtaactcgt tca                                          23

<210> SEQ ID NO 211
<211> LENGTH: 24
<212> TYPE: DNA
<213> ORGANISM: Artificial Sequence
<220> FEATURE:
<223> OTHER INFORMATION: Primer
```

```
<400> SEQUENCE: 211
acacaatcac atgatccgtt atcg                                              24

<210> SEQ ID NO 212
<211> LENGTH: 24
<212> TYPE: DNA
<213> ORGANISM: Artificial Sequence
<220> FEATURE:
<223> OTHER INFORMATION: Primer

<400> SEQUENCE: 212
agtatgcagt tgtaactcgc tcta                                              24

<210> SEQ ID NO 213
<211> LENGTH: 22
<212> TYPE: DNA
<213> ORGANISM: Artificial Sequence
<220> FEATURE:
<223> OTHER INFORMATION: Primer

<400> SEQUENCE: 213
caccaccacc agaaacgata ac                                                22

<210> SEQ ID NO 214
<211> LENGTH: 18
<212> TYPE: DNA
<213> ORGANISM: Artificial Sequence
<220> FEATURE:
<223> OTHER INFORMATION: Primer

<400> SEQUENCE: 214
gtgattggtt gcggtcca                                                     18

<210> SEQ ID NO 215
<211> LENGTH: 18
<212> TYPE: DNA
<213> ORGANISM: Artificial Sequence
<220> FEATURE:
<223> OTHER INFORMATION: Primer

<400> SEQUENCE: 215
cccgccacca gacactat                                                     18

<210> SEQ ID NO 216
<211> LENGTH: 22
<212> TYPE: DNA
<213> ORGANISM: Artificial Sequence
<220> FEATURE:
<223> OTHER INFORMATION: Primer

<400> SEQUENCE: 216
ygagaatgga gtaattggct ct                                                22

<210> SEQ ID NO 217
<211> LENGTH: 24
<212> TYPE: DNA
<213> ORGANISM: Artificial Sequence
<220> FEATURE:
<223> OTHER INFORMATION: Primer

<400> SEQUENCE: 217
watttcacca ccaccagaaa caaa                                              24
```

<210> SEQ ID NO 218
<211> LENGTH: 18
<212> TYPE: DNA
<213> ORGANISM: Artificial Sequence
<220> FEATURE:
<223> OTHER INFORMATION: Primer

<400> SEQUENCE: 218
gggwgccaat cgggttat                                                 18

<210> SEQ ID NO 219
<211> LENGTH: 18
<212> TYPE: DNA
<213> ORGANISM: Artificial Sequence
<220> FEATURE:
<223> OTHER INFORMATION: Primer

<400> SEQUENCE: 219
ctcagtgagt ctgcgaaa                                                 18

<210> SEQ ID NO 220
<211> LENGTH: 18
<212> TYPE: DNA
<213> ORGANISM: Artificial Sequence
<220> FEATURE:
<223> OTHER INFORMATION: Primer

<400> SEQUENCE: 220
ctcggtgagc ctgcgaaa                                                 18

<210> SEQ ID NO 221
<211> LENGTH: 21
<212> TYPE: DNA
<213> ORGANISM: Artificial Sequence
<220> FEATURE:
<223> OTHER INFORMATION: Primer

<400> SEQUENCE: 221
aaagactacg agcagaatgg c                                             21

<210> SEQ ID NO 222
<211> LENGTH: 24
<212> TYPE: DNA
<213> ORGANISM: Artificial Sequence
<220> FEATURE:
<223> OTHER INFORMATION: Primer

<400> SEQUENCE: 222
acggtaagtg aagtaagtgt gaag                                          24

<210> SEQ ID NO 223
<211> LENGTH: 19
<212> TYPE: DNA
<213> ORGANISM: Artificial Sequence
<220> FEATURE:
<223> OTHER INFORMATION: Primer

<400> SEQUENCE: 223
aacgctgcca ttgttacca                                                19

<210> SEQ ID NO 224
<211> LENGTH: 21
<212> TYPE: DNA
<213> ORGANISM: Artificial Sequence
<220> FEATURE:
<223> OTHER INFORMATION: Primer

```
<400> SEQUENCE: 224
aagccttgaa gtgttctgga g                                              21

<210> SEQ ID NO 225
<211> LENGTH: 23
<212> TYPE: DNA
<213> ORGANISM: Artificial Sequence
<220> FEATURE:
<223> OTHER INFORMATION: Primer

<400> SEQUENCE: 225
aagacaggag gtatcggatt tga                                            23

<210> SEQ ID NO 226
<211> LENGTH: 22
<212> TYPE: DNA
<213> ORGANISM: Artificial Sequence
<220> FEATURE:
<223> OTHER INFORMATION: Primer

<400> SEQUENCE: 226
cgtaggcagc taagttctcg ta                                             22

<210> SEQ ID NO 227
<211> LENGTH: 23
<212> TYPE: DNA
<213> ORGANISM: Artificial Sequence
<220> FEATURE:
<223> OTHER INFORMATION: Primer

<400> SEQUENCE: 227
aagaccgcat caatatcgtc atc                                            23

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
catagcaagc cgtccaagaa                                                20

<210> SEQ ID NO 229
<211> LENGTH: 24
<212> TYPE: DNA
<213> ORGANISM: Artificial Sequence
<220> FEATURE:
<223> OTHER INFORMATION: Primer

<400> SEQUENCE: 229
aagactctta cgaaccatgt tgtt                                           24

<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230
cctctggctc ggaatctatt g                                              21
```

```
<210> SEQ ID NO 231
<211> LENGTH: 23
<212> TYPE: DNA
<213> ORGANISM: Artificial Sequence
<220> FEATURE:
<223> OTHER INFORMATION: Primer

<400> SEQUENCE: 231
aagcactgac ctataaccaa tgg                                           23

<210> SEQ ID NO 232
<211> LENGTH: 22
<212> TYPE: DNA
<213> ORGANISM: Artificial Sequence
<220> FEATURE:
<223> OTHER INFORMATION: Primer

<400> SEQUENCE: 232
cccaggaatg ttcggaaaga aa                                            22

<210> SEQ ID NO 233
<211> LENGTH: 22
<212> TYPE: DNA
<213> ORGANISM: Artificial Sequence
<220> FEATURE:
<223> OTHER INFORMATION: Primer

<400> SEQUENCE: 233
aagcattcag agacacaacc aa                                            22

<210> SEQ ID NO 234
<211> LENGTH: 21
<212> TYPE: DNA
<213> ORGANISM: Artificial Sequence
<220> FEATURE:
<223> OTHER INFORMATION: Primer

<400> SEQUENCE: 234
aaccaacacc accaatgaca t                                             21

<210> SEQ ID NO 235
<211> LENGTH: 24
<212> TYPE: DNA
<213> ORGANISM: Artificial Sequence
<220> FEATURE:
<223> OTHER INFORMATION: Primer

<400> SEQUENCE: 235
aaggtgagca gctaatcttt aagg                                          24

<210> SEQ ID NO 236
<211> LENGTH: 24
<212> TYPE: DNA
<213> ORGANISM: Artificial Sequence
<220> FEATURE:
<223> OTHER INFORMATION: Primer

<400> SEQUENCE: 236
tgaccctgaa attccattct ttga                                          24

<210> SEQ ID NO 237
<211> LENGTH: 22
<212> TYPE: DNA
<213> ORGANISM: Artificial Sequence
<220> FEATURE:
<223> OTHER INFORMATION: Primer
```

<400> SEQUENCE: 237
aagtcgcaca acatcttgaa gg					22

<210> SEQ ID NO 238
<211> LENGTH: 24
<212> TYPE: DNA
<213> ORGANISM: Artificial Sequence
<220> FEATURE:
<223> OTHER INFORMATION: Primer

<400> SEQUENCE: 238
agatttgagc accaccaata atga					24

<210> SEQ ID NO 239
<211> LENGTH: 24
<212> TYPE: DNA
<213> ORGANISM: Artificial Sequence
<220> FEATURE:
<223> OTHER INFORMATION: Primer

<400> SEQUENCE: 239
aatcaatatc acgacagcga tcaa					24

<210> SEQ ID NO 240
<211> LENGTH: 19
<212> TYPE: DNA
<213> ORGANISM: Artificial Sequence
<220> FEATURE:
<223> OTHER INFORMATION: Primer

<400> SEQUENCE: 240
cttcacggga tgggtctca					19

<210> SEQ ID NO 241
<211> LENGTH: 20
<212> TYPE: DNA
<213> ORGANISM: Artificial Sequence
<220> FEATURE:
<223> OTHER INFORMATION: Primer

<400> SEQUENCE: 241
aatcagtggc tccttgttgg					20

<210> SEQ ID NO 242
<211> LENGTH: 24
<212> TYPE: DNA
<213> ORGANISM: Artificial Sequence
<220> FEATURE:
<223> OTHER INFORMATION: Primer

<400> SEQUENCE: 242
ggaagaacac ccatagagtc aaat					24

<210> SEQ ID NO 243
<211> LENGTH: 20
<212> TYPE: DNA
<213> ORGANISM: Artificial Sequence
<220> FEATURE:
<223> OTHER INFORMATION: Primer

<400> SEQUENCE: 243
aatcagtggc ttcttgtcgg					20

-continued

```
<210> SEQ ID NO 244
<211> LENGTH: 24
<212> TYPE: DNA
<213> ORGANISM: Artificial Sequence
<220> FEATURE:
<223> OTHER INFORMATION: Primer

<400> SEQUENCE: 244
gtggatgata gataagtgga tggt                                              24

<210> SEQ ID NO 245
<211> LENGTH: 20
<212> TYPE: DNA
<213> ORGANISM: Artificial Sequence
<220> FEATURE:
<223> OTHER INFORMATION: Primer

<400> SEQUENCE: 245
aatggcgtaa tcggtagtgg                                                   20

<210> SEQ ID NO 246
<211> LENGTH: 23
<212> TYPE: DNA
<213> ORGANISM: Artificial Sequence
<220> FEATURE:
<223> OTHER INFORMATION: Primer

<400> SEQUENCE: 246
gcttgaaatt ccgttctttg aca                                               23

<210> SEQ ID NO 247
<211> LENGTH: 19
<212> TYPE: DNA
<213> ORGANISM: Artificial Sequence
<220> FEATURE:
<223> OTHER INFORMATION: Primer

<400> SEQUENCE: 247
acgcattgct gtcattggt                                                    19

<210> SEQ ID NO 248
<211> LENGTH: 18
<212> TYPE: DNA
<213> ORGANISM: Artificial Sequence
<220> FEATURE:
<223> OTHER INFORMATION: Primer

<400> SEQUENCE: 248
ctcgctggca ctggaatc                                                     18

<210> SEQ ID NO 249
<211> LENGTH: 19
<212> TYPE: DNA
<213> ORGANISM: Artificial Sequence
<220> FEATURE:
<223> OTHER INFORMATION: Primer

<400> SEQUENCE: 249
actctatgcc gaggctctg                                                    19

<210> SEQ ID NO 250
<211> LENGTH: 20
<212> TYPE: DNA
<213> ORGANISM: Artificial Sequence
<220> FEATURE:
<223> OTHER INFORMATION: Primer
```

<400> SEQUENCE: 250
cgctgacgac tcaaggtaac                                              20

<210> SEQ ID NO 251
<211> LENGTH: 18
<212> TYPE: DNA
<213> ORGANISM: Artificial Sequence
<220> FEATURE:
<223> OTHER INFORMATION: Primer

<400> SEQUENCE: 251
watgggagat cgcgtgcg                                                18

<210> SEQ ID NO 252
<211> LENGTH: 20
<212> TYPE: DNA
<213> ORGANISM: Artificial Sequence
<220> FEATURE:
<223> OTHER INFORMATION: Primer

<400> SEQUENCE: 252
gcwgtaccac ccgacaatct                                              20

<210> SEQ ID NO 253
<211> LENGTH: 18
<212> TYPE: DNA
<213> ORGANISM: Artificial Sequence
<220> FEATURE:
<223> OTHER INFORMATION: Primer

<400> SEQUENCE: 253
gcagggtcaa gtygtcgg                                                18

<210> SEQ ID NO 254
<211> LENGTH: 18
<212> TYPE: DNA
<213> ORGANISM: Artificial Sequence
<220> FEATURE:
<223> OTHER INFORMATION: Primer

<400> SEQUENCE: 254
tcggactcga csgcatag                                                18

<210> SEQ ID NO 255
<211> LENGTH: 18
<212> TYPE: DNA
<213> ORGANISM: Artificial Sequence
<220> FEATURE:
<223> OTHER INFORMATION: Primer

<400> SEQUENCE: 255
acccgacaac ttgaccct                                                18

<210> SEQ ID NO 256
<211> LENGTH: 21
<212> TYPE: DNA
<213> ORGANISM: Artificial Sequence
<220> FEATURE:
<223> OTHER INFORMATION: Primer

<400> SEQUENCE: 256
accaacacaa caatggagtc a                                            21

```
<210> SEQ ID NO 257
<211> LENGTH: 19
<212> TYPE: DNA
<213> ORGANISM: Artificial Sequence
<220> FEATURE:
<223> OTHER INFORMATION: Primer

<400> SEQUENCE: 257
aatctcaccc aggctcagt                                                  19

<210> SEQ ID NO 258
<211> LENGTH: 18
<212> TYPE: DNA
<213> ORGANISM: Artificial Sequence
<220> FEATURE:
<223> OTHER INFORMATION: Primer

<400> SEQUENCE: 258
ccgttcaagc gcagtcat                                                   18

<210> SEQ ID NO 259
<211> LENGTH: 20
<212> TYPE: DNA
<213> ORGANISM: Artificial Sequence
<220> FEATURE:
<223> OTHER INFORMATION: Primer

<400> SEQUENCE: 259
gctggtggtt atgcactcag                                                 20

<210> SEQ ID NO 260
<211> LENGTH: 19
<212> TYPE: DNA
<213> ORGANISM: Artificial Sequence
<220> FEATURE:
<223> OTHER INFORMATION: Primer

<400> SEQUENCE: 260
cgcccaagaa ggatttccg                                                  19

<210> SEQ ID NO 261
<211> LENGTH: 19
<212> TYPE: DNA
<213> ORGANISM: Artificial Sequence
<220> FEATURE:
<223> OTHER INFORMATION: Primer

<400> SEQUENCE: 261
cgtgctgtcg aaccttcaa                                                  19

<210> SEQ ID NO 262
<211> LENGTH: 21
<212> TYPE: DNA
<213> ORGANISM: Artificial Sequence
<220> FEATURE:
<223> OTHER INFORMATION: Primer

<400> SEQUENCE: 262
gctggaccca gatcctttac a                                               21

<210> SEQ ID NO 263
<211> LENGTH: 22
<212> TYPE: DNA
<213> ORGANISM: Artificial Sequence
<220> FEATURE:
<223> OTHER INFORMATION: Primer
```

<400> SEQUENCE: 263
catcattttc ggcatcgtca ac         22

<210> SEQ ID NO 264
<211> LENGTH: 18
<212> TYPE: DNA
<213> ORGANISM: Artificial Sequence
<220> FEATURE:
<223> OTHER INFORMATION: Primer

<400> SEQUENCE: 264
gcgacaaggc ataggctt         18

<210> SEQ ID NO 265
<211> LENGTH: 22
<212> TYPE: DNA
<213> ORGANISM: Artificial Sequence
<220> FEATURE:
<223> OTHER INFORMATION: Primer

<400> SEQUENCE: 265
gtcaacataa cctcggacag tt         22

<210> SEQ ID NO 266
<211> LENGTH: 18
<212> TYPE: DNA
<213> ORGANISM: Artificial Sequence
<220> FEATURE:
<223> OTHER INFORMATION: Primer

<400> SEQUENCE: 266
ctcggccatc agcttacg         18

<210> SEQ ID NO 267
<211> LENGTH: 24
<212> TYPE: DNA
<213> ORGANISM: Artificial Sequence
<220> FEATURE:
<223> OTHER INFORMATION: Primer

<400> SEQUENCE: 267
aaagccttaa tgacaggttt gagt         24

<210> SEQ ID NO 268
<211> LENGTH: 24
<212> TYPE: DNA
<213> ORGANISM: Artificial Sequence
<220> FEATURE:
<223> OTHER INFORMATION: Primer

<400> SEQUENCE: 268
gaagatggag cagatgtgat tgat         24

<210> SEQ ID NO 269
<211> LENGTH: 23
<212> TYPE: DNA
<213> ORGANISM: Artificial Sequence
<220> FEATURE:
<223> OTHER INFORMATION: Primer

<400> SEQUENCE: 269
ggcaaagtca gattgcaaac ttg         23

```
<210> SEQ ID NO 270
<211> LENGTH: 22
<212> TYPE: DNA
<213> ORGANISM: Artificial Sequence
<220> FEATURE:
<223> OTHER INFORMATION: Primer

<400> SEQUENCE: 270
cctcttccgg attcgtttca ac                                      22

<210> SEQ ID NO 271
<211> LENGTH: 23
<212> TYPE: DNA
<213> ORGANISM: Artificial Sequence
<220> FEATURE:
<223> OTHER INFORMATION: Primer

<400> SEQUENCE: 271
ccaggtccta atgctgatag acg                                     23

<210> SEQ ID NO 272
<211> LENGTH: 24
<212> TYPE: DNA
<213> ORGANISM: Artificial Sequence
<220> FEATURE:
<223> OTHER INFORMATION: Primer

<400> SEQUENCE: 272
accgtcgttt acgttctgta ggtg                                    24

<210> SEQ ID NO 273
<211> LENGTH: 23
<212> TYPE: DNA
<213> ORGANISM: Artificial Sequence
<220> FEATURE:
<223> OTHER INFORMATION: Primer

<400> SEQUENCE: 273
ccaggtccta atgctgatag acg                                     23

<210> SEQ ID NO 274
<211> LENGTH: 22
<212> TYPE: DNA
<213> ORGANISM: Artificial Sequence
<220> FEATURE:
<223> OTHER INFORMATION: Primer

<400> SEQUENCE: 274
ggaccaagca aayccattag ct                                      22

<210> SEQ ID NO 275
<211> LENGTH: 21
<212> TYPE: DNA
<213> ORGANISM: Artificial Sequence
<220> FEATURE:
<223> OTHER INFORMATION: Primer

<400> SEQUENCE: 275
gtgaaggcat ccaatsaact t                                       21

<210> SEQ ID NO 276
<211> LENGTH: 24
<212> TYPE: DNA
<213> ORGANISM: Artificial Sequence
<220> FEATURE:
<223> OTHER INFORMATION: Primer
```

<400> SEQUENCE: 276
aaacmacaaa gagaacacag agat                                    24

<210> SEQ ID NO 277
<211> LENGTH: 24
<212> TYPE: DNA
<213> ORGANISM: Artificial Sequence
<220> FEATURE:
<223> OTHER INFORMATION: Primer

<400> SEQUENCE: 277
ggaacgatgc ctatctcata tgct                                    24

<210> SEQ ID NO 278
<211> LENGTH: 25
<212> TYPE: DNA
<213> ORGANISM: Artificial Sequence
<220> FEATURE:
<223> OTHER INFORMATION: Primer

<400> SEQUENCE: 278
atagcgtcat tattccagga atgca                                   25

<210> SEQ ID NO 279
<211> LENGTH: 19
<212> TYPE: DNA
<213> ORGANISM: Artificial Sequence
<220> FEATURE:
<223> OTHER INFORMATION: Primer

<400> SEQUENCE: 279
cggctcgact tcctgatga                                          19

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
tgtgcggtat tgggaaacag                                         20

<210> SEQ ID NO 281
<211> LENGTH: 25
<212> TYPE: DNA
<213> ORGANISM: Artificial Sequence
<220> FEATURE:
<223> OTHER INFORMATION: Primer

<400> SEQUENCE: 281
gccacactat cataaccact accga                                   25

<210> SEQ ID NO 282
<211> LENGTH: 25
<212> TYPE: DNA
<213> ORGANISM: Artificial Sequence
<220> FEATURE:
<223> OTHER INFORMATION: Primer

<400> SEQUENCE: 282
tccaagagca ataagggcat accaa                                   25

```
<210> SEQ ID NO 283
<211> LENGTH: 20
<212> TYPE: DNA
<213> ORGANISM: Artificial Sequence
<220> FEATURE:
<223> OTHER INFORMATION: Primer

<400> SEQUENCE: 283
acactcttgg cggtttcact                                          20

<210> SEQ ID NO 284
<211> LENGTH: 24
<212> TYPE: DNA
<213> ORGANISM: Artificial Sequence
<220> FEATURE:
<223> OTHER INFORMATION: Primer

<400> SEQUENCE: 284
cctaagggcc aatctgaacc tatt                                     24

<210> SEQ ID NO 285
<211> LENGTH: 27
<212> TYPE: DNA
<213> ORGANISM: Artificial Sequence
<220> FEATURE:
<223> OTHER INFORMATION: Primer

<400> SEQUENCE: 285
caaccattga tttcaaagaa ggactac                                  27

<210> SEQ ID NO 286
<211> LENGTH: 21
<212> TYPE: DNA
<213> ORGANISM: Artificial Sequence
<220> FEATURE:
<223> OTHER INFORMATION: Primer

<400> SEQUENCE: 286
tcaaagcctg tcggaattgg t                                        21

<210> SEQ ID NO 287
<211> LENGTH: 28
<212> TYPE: DNA
<213> ORGANISM: Artificial Sequence
<220> FEATURE:
<223> OTHER INFORMATION: Primer

<400> SEQUENCE: 287
atttaatcgt ggaatacgag tttgctaa                                 28

<210> SEQ ID NO 288
<211> LENGTH: 24
<212> TYPE: DNA
<213> ORGANISM: Artificial Sequence
<220> FEATURE:
<223> OTHER INFORMATION: Primer

<400> SEQUENCE: 288
cgtcaattcc tgcatgtttt aagg                                     24

<210> SEQ ID NO 289
<211> LENGTH: 24
<212> TYPE: DNA
<213> ORGANISM: Artificial Sequence
<220> FEATURE:
<223> OTHER INFORMATION: Primer
```

```
<400> SEQUENCE: 289
agtttgagct gtcttggttc attg                                          24

<210> SEQ ID NO 290
<211> LENGTH: 24
<212> TYPE: DNA
<213> ORGANISM: Artificial Sequence
<220> FEATURE:
<223> OTHER INFORMATION: Primer

<400> SEQUENCE: 290
tgcagcagat cctactcctt gtac                                          24

<210> SEQ ID NO 291
<211> LENGTH: 25
<212> TYPE: DNA
<213> ORGANISM: Artificial Sequence
<220> FEATURE:
<223> OTHER INFORMATION: Primer

<400> SEQUENCE: 291
ctttctgggc ttccattggt ttatc                                         25

<210> SEQ ID NO 292
<211> LENGTH: 22
<212> TYPE: DNA
<213> ORGANISM: Artificial Sequence
<220> FEATURE:
<223> OTHER INFORMATION: Primer

<400> SEQUENCE: 292
cgagctctca tactgcattc ca                                            22

<210> SEQ ID NO 293
<211> LENGTH: 26
<212> TYPE: DNA
<213> ORGANISM: Artificial Sequence
<220> FEATURE:
<223> OTHER INFORMATION: Primer

<400> SEQUENCE: 293
cttcttccaa atgttccatt cttttt                                        26

<210> SEQ ID NO 294
<211> LENGTH: 24
<212> TYPE: DNA
<213> ORGANISM: Artificial Sequence
<220> FEATURE:
<223> OTHER INFORMATION: Primer

<400> SEQUENCE: 294
accagatcgt ttaagtgcat caaa                                          24

<210> SEQ ID NO 295
<211> LENGTH: 20
<212> TYPE: DNA
<213> ORGANISM: Artificial Sequence
<220> FEATURE:
<223> OTHER INFORMATION: Primer

<400> SEQUENCE: 295
aacgaagggc aggtagaagc                                               20
```

```
<210> SEQ ID NO 296
<211> LENGTH: 20
<212> TYPE: DNA
<213> ORGANISM: Artificial Sequence
<220> FEATURE:
<223> OTHER INFORMATION: Primer

<400> SEQUENCE: 296
tgaccacaag cagcgtcaat                                                  20

<210> SEQ ID NO 297
<211> LENGTH: 21
<212> TYPE: DNA
<213> ORGANISM: Artificial Sequence
<220> FEATURE:
<223> OTHER INFORMATION: Primer

<400> SEQUENCE: 297
gtgaggaacg cagcaaattg a                                                21

<210> SEQ ID NO 298
<211> LENGTH: 20
<212> TYPE: DNA
<213> ORGANISM: Artificial Sequence
<220> FEATURE:
<223> OTHER INFORMATION: Primer

<400> SEQUENCE: 298
gcttctacct gcccttcgtt                                                  20

<210> SEQ ID NO 299
<211> LENGTH: 19
<212> TYPE: DNA
<213> ORGANISM: Artificial Sequence
<220> FEATURE:
<223> OTHER INFORMATION: Primer

<400> SEQUENCE: 299
ggatcaaacg gcctgcaca                                                   19

<210> SEQ ID NO 300
<211> LENGTH: 22
<212> TYPE: DNA
<213> ORGANISM: Artificial Sequence
<220> FEATURE:
<223> OTHER INFORMATION: Primer

<400> SEQUENCE: 300
tggctccaat ggtytacacc aa                                               22

<210> SEQ ID NO 301
<211> LENGTH: 29
<212> TYPE: DNA
<213> ORGANISM: Artificial Sequence
<220> FEATURE:
<223> OTHER INFORMATION: Primer

<400> SEQUENCE: 301
gtcaaaaatc atgaacctca ttacttatg                                        29

<210> SEQ ID NO 302
<211> LENGTH: 29
<212> TYPE: DNA
<213> ORGANISM: Artificial Sequence
<220> FEATURE:
<223> OTHER INFORMATION: Primer
```

<400> SEQUENCE: 302
atttcatata tgtaattcct ccacatctc      29

<210> SEQ ID NO 303
<211> LENGTH: 29
<212> TYPE: DNA
<213> ORGANISM: Artificial Sequence
<220> FEATURE:
<223> OTHER INFORMATION: Primer

<400> SEQUENCE: 303
caaatattat ctcgtaattt accttgttc      29

<210> SEQ ID NO 304
<211> LENGTH: 29
<212> TYPE: DNA
<213> ORGANISM: Artificial Sequence
<220> FEATURE:
<223> OTHER INFORMATION: Primer

<400> SEQUENCE: 304
ctctgcttta tattataaaa ttacggctg      29

<210> SEQ ID NO 305
<211> LENGTH: 27
<212> TYPE: DNA
<213> ORGANISM: Artificial Sequence
<220> FEATURE:
<223> OTHER INFORMATION: Primer

<400> SEQUENCE: 305
cactttttat tcttcaaaga tttgagc       27

<210> SEQ ID NO 306
<211> LENGTH: 21
<212> TYPE: DNA
<213> ORGANISM: Artificial Sequence
<220> FEATURE:
<223> OTHER INFORMATION: Primer

<400> SEQUENCE: 306
ctcatgttac aratacttgc g       21

<210> SEQ ID NO 307
<211> LENGTH: 21
<212> TYPE: DNA
<213> ORGANISM: Artificial Sequence
<220> FEATURE:
<223> OTHER INFORMATION: Primer

<400> SEQUENCE: 307
ccttgataat agccttcttg g       21

<210> SEQ ID NO 308
<211> LENGTH: 26
<212> TYPE: DNA
<213> ORGANISM: Artificial Sequence
<220> FEATURE:
<223> OTHER INFORMATION: Primer

<400> SEQUENCE: 308
cgttataagt gtacgaatgg tttttg       26

<210> SEQ ID NO 309
<211> LENGTH: 21
<212> TYPE: DNA
<213> ORGANISM: Artificial Sequence
<220> FEATURE:
<223> OTHER INFORMATION: Primer

<400> SEQUENCE: 309
tcatctgcag aatgggaagt t                                            21

<210> SEQ ID NO 310
<211> LENGTH: 20
<212> TYPE: DNA
<213> ORGANISM: Artificial Sequence
<220> FEATURE:
<223> OTHER INFORMATION: Primer

<400> SEQUENCE: 310
gaagctttgg gcgataaaga                                              20

<210> SEQ ID NO 311
<211> LENGTH: 23
<212> TYPE: DNA
<213> ORGANISM: Artificial Sequence
<220> FEATURE:
<223> OTHER INFORMATION: Primer

<400> SEQUENCE: 311
gcactgtctc gtttagacca atc                                          23

<210> SEQ ID NO 312
<211> LENGTH: 24
<212> TYPE: DNA
<213> ORGANISM: Artificial Sequence
<220> FEATURE:
<223> OTHER INFORMATION: Primer

<400> SEQUENCE: 312
tccagtctat aaaggstatg tcag                                         24

<210> SEQ ID NO 313
<211> LENGTH: 24
<212> TYPE: DNA
<213> ORGANISM: Artificial Sequence
<220> FEATURE:
<223> OTHER INFORMATION: Primer

<400> SEQUENCE: 313
acttataatg gcttcatgct tacc                                         24

<210> SEQ ID NO 314
<211> LENGTH: 22
<212> TYPE: DNA
<213> ORGANISM: Artificial Sequence
<220> FEATURE:
<223> OTHER INFORMATION: Primer

<400> SEQUENCE: 314
accacaaaca cacttaaaga tg                                           22

<210> SEQ ID NO 315
<211> LENGTH: 25
<212> TYPE: DNA
<213> ORGANISM: Artificial Sequence
<220> FEATURE:
<223> OTHER INFORMATION: Primer

<400> SEQUENCE: 315
caatttcaag tatttggtcc ataac    25

<210> SEQ ID NO 316
<211> LENGTH: 22
<212> TYPE: DNA
<213> ORGANISM: Artificial Sequence
<220> FEATURE:
<223> OTHER INFORMATION: Primer

<400> SEQUENCE: 316
aacacaacga acacattgaa ag    22

<210> SEQ ID NO 317
<211> LENGTH: 22
<212> TYPE: DNA
<213> ORGANISM: Artificial Sequence
<220> FEATURE:
<223> OTHER INFORMATION: Primer

<400> SEQUENCE: 317
cgtatttctc aatcacatca gc    22

<210> SEQ ID NO 318
<211> LENGTH: 24
<212> TYPE: DNA
<213> ORGANISM: Artificial Sequence
<220> FEATURE:
<223> OTHER INFORMATION: Primer

<400> SEQUENCE: 318
cgaagtatag acactggagc gata    24

<210> SEQ ID NO 319
<211> LENGTH: 19
<212> TYPE: DNA
<213> ORGANISM: Artificial Sequence
<220> FEATURE:
<223> OTHER INFORMATION: Primer

<400> SEQUENCE: 319
gcgactctct tggcgttta    19

<210> SEQ ID NO 320
<211> LENGTH: 22
<212> TYPE: DNA
<213> ORGANISM: Artificial Sequence
<220> FEATURE:
<223> OTHER INFORMATION: Primer

<400> SEQUENCE: 320
tcagttcatt gctcacgata tg    22

<210> SEQ ID NO 321
<211> LENGTH: 20
<212> TYPE: DNA
<213> ORGANISM: Artificial Sequence
<220> FEATURE:
<223> OTHER INFORMATION: Primer

<400> SEQUENCE: 321
gccaacggct acagtgataa    20

```
<210> SEQ ID NO 322
<211> LENGTH: 24
<212> TYPE: DNA
<213> ORGANISM: Artificial Sequence
<220> FEATURE:
<223> OTHER INFORMATION: Primer

<400> SEQUENCE: 322
caggatattt tcaaactcc ttca                                          24

<210> SEQ ID NO 323
<211> LENGTH: 20
<212> TYPE: DNA
<213> ORGANISM: Artificial Sequence
<220> FEATURE:
<223> OTHER INFORMATION: Primer

<400> SEQUENCE: 323
tggaggacca aggatattcg                                              20

<210> SEQ ID NO 324
<211> LENGTH: 27
<212> TYPE: DNA
<213> ORGANISM: Artificial Sequence
<220> FEATURE:
<223> OTHER INFORMATION: Primer

<400> SEQUENCE: 324
cctttgaatg ccctccatga ataaaat                                      27

<210> SEQ ID NO 325
<211> LENGTH: 29
<212> TYPE: DNA
<213> ORGANISM: Artificial Sequence
<220> FEATURE:
<223> OTHER INFORMATION: Primer

<400> SEQUENCE: 325
gcatatagaa aagatagaag ttcgaaaga                                    29

<210> SEQ ID NO 326
<211> LENGTH: 27
<212> TYPE: DNA
<213> ORGANISM: Artificial Sequence
<220> FEATURE:
<223> OTHER INFORMATION: Primer

<400> SEQUENCE: 326
tatggctaga cggtaaacaa aatacag                                      27

<210> SEQ ID NO 327
<211> LENGTH: 26
<212> TYPE: DNA
<213> ORGANISM: Artificial Sequence
<220> FEATURE:
<223> OTHER INFORMATION: Primer

<400> SEQUENCE: 327
ctctgaacct tcccatcaaa aacatc                                       26

<210> SEQ ID NO 328
<211> LENGTH: 25
<212> TYPE: DNA
<213> ORGANISM: Artificial Sequence
<220> FEATURE:
<223> OTHER INFORMATION: Primer
```

-continued

<400> SEQUENCE: 328
ttactgttmg ggtatttgaa gatgg                                   25

<210> SEQ ID NO 329
<211> LENGTH: 21
<212> TYPE: DNA
<213> ORGANISM: Artificial Sequence
<220> FEATURE:
<223> OTHER INFORMATION: Primer

<400> SEQUENCE: 329
ccgtttcata aggygagttg t                                       21

<210> SEQ ID NO 330
<211> LENGTH: 20
<212> TYPE: DNA
<213> ORGANISM: Artificial Sequence
<220> FEATURE:
<223> OTHER INFORMATION: Primer

<400> SEQUENCE: 330
atgtcagagg gatagatcca                                         20

<210> SEQ ID NO 331
<211> LENGTH: 23
<212> TYPE: DNA
<213> ORGANISM: Artificial Sequence
<220> FEATURE:
<223> OTHER INFORMATION: Primer

<400> SEQUENCE: 331
tatagctact gtcaccagac aat                                     23

<210> SEQ ID NO 332
<211> LENGTH: 22
<212> TYPE: DNA
<213> ORGANISM: Artificial Sequence
<220> FEATURE:
<223> OTHER INFORMATION: Primer

<400> SEQUENCE: 332
agttctgcgt tttgtcactg tc                                      22

<210> SEQ ID NO 333
<211> LENGTH: 19
<212> TYPE: DNA
<213> ORGANISM: Artificial Sequence
<220> FEATURE:
<223> OTHER INFORMATION: Primer

<400> SEQUENCE: 333
cggaagcaca ttgctgatt                                          19

<210> SEQ ID NO 334
<211> LENGTH: 26
<212> TYPE: DNA
<213> ORGANISM: Artificial Sequence
<220> FEATURE:
<223> OTHER INFORMATION: Primer

<400> SEQUENCE: 334
gatacattaa gacgcctaaa ggatgc                                  26

```
<210> SEQ ID NO 335
<211> LENGTH: 23
<212> TYPE: DNA
<213> ORGANISM: Artificial Sequence
<220> FEATURE:
<223> OTHER INFORMATION: Primer

<400> SEQUENCE: 335 cctttttgacc aattcggaca act                                          23

<210> SEQ ID NO 336
<211> LENGTH: 26
<212> TYPE: DNA
<213> ORGANISM: Artificial Sequence
<220> FEATURE:
<223> OTHER INFORMATION: Primer

<400> SEQUENCE: 336
tggaataatc atcatcatta cagcca                                        26

<210> SEQ ID NO 337
<211> LENGTH: 26
<212> TYPE: DNA
<213> ORGANISM: Artificial Sequence
<220> FEATURE:
<223> OTHER INFORMATION: Primer

<400> SEQUENCE: 337
gagtcatatc acgatcttat tctggc                                        26

<210> SEQ ID NO 338
<211> LENGTH: 21
<212> TYPE: DNA
<213> ORGANISM: Artificial Sequence
<220> FEATURE:
<223> OTHER INFORMATION: Primer

<400> SEQUENCE: 338
taccagtctg cgtctgattc c                                             21

<210> SEQ ID NO 339
<211> LENGTH: 21
<212> TYPE: DNA
<213> ORGANISM: Artificial Sequence
<220> FEATURE:
<223> OTHER INFORMATION: Primer

<400> SEQUENCE: 339
acgttgcgct cattacttct g                                             21

<210> SEQ ID NO 340
<211> LENGTH: 23
<212> TYPE: DNA
<213> ORGANISM: Artificial Sequence
<220> FEATURE:
<223> OTHER INFORMATION: Primer

<400> SEQUENCE: 340
tgagttacct gaatcactgg aag                                           23

<210> SEQ ID NO 341
<211> LENGTH: 21
<212> TYPE: DNA
<213> ORGANISM: Artificial Sequence
<220> FEATURE:
<223> OTHER INFORMATION: Primer
```

<400> SEQUENCE: 341
tcgaggatga tagtgcaggt c                                              21

<210> SEQ ID NO 342
<211> LENGTH: 21
<212> TYPE: DNA
<213> ORGANISM: Artificial Sequence
<220> FEATURE:
<223> OTHER INFORMATION: Primer

<400> SEQUENCE: 342
ctgcgttagg tggaatacca t                                              21

<210> SEQ ID NO 343
<211> LENGTH: 24
<212> TYPE: DNA
<213> ORGANISM: Artificial Sequence
<220> FEATURE:
<223> OTHER INFORMATION: Primer

<400> SEQUENCE: 343
ctgggtctcc tcattacaag tatc                                           24

<210> SEQ ID NO 344
<211> LENGTH: 18
<212> TYPE: DNA
<213> ORGANISM: Artificial Sequence
<220> FEATURE:
<223> OTHER INFORMATION: Primer

<400> SEQUENCE: 344
gttccagcct gccatctg                                                  18

<210> SEQ ID NO 345
<211> LENGTH: 18
<212> TYPE: DNA
<213> ORGANISM: Artificial Sequence
<220> FEATURE:
<223> OTHER INFORMATION: Primer

<400> SEQUENCE: 345
tcgccagcaa cacttcag                                                  18

<210> SEQ ID NO 346
<211> LENGTH: 18
<212> TYPE: DNA
<213> ORGANISM: Artificial Sequence
<220> FEATURE:
<223> OTHER INFORMATION: Primer

<400> SEQUENCE: 346
aagcacgctg gtggttac                                                  18

<210> SEQ ID NO 347
<211> LENGTH: 19
<212> TYPE: DNA
<213> ORGANISM: Artificial Sequence
<220> FEATURE:
<223> OTHER INFORMATION: Primer

<400> SEQUENCE: 347
ctggatggtg ttggtggaa                                                 19

<210> SEQ ID NO 348
<211> LENGTH: 20
<212> TYPE: DNA
<213> ORGANISM: Artificial Sequence
<220> FEATURE:
<223> OTHER INFORMATION: Primer

<400> SEQUENCE: 348
cgcgagygct ttctatcttg                                                 20

<210> SEQ ID NO 349
<211> LENGTH: 20
<212> TYPE: DNA
<213> ORGANISM: Artificial Sequence
<220> FEATURE:
<223> OTHER INFORMATION: Primer

<400> SEQUENCE: 349
gagasccact ggttccagaa                                                 20

<210> SEQ ID NO 350
<211> LENGTH: 43
<212> TYPE: DNA
<213> ORGANISM: Artificial Sequence
<220> FEATURE:
<223> OTHER INFORMATION: Primer

<400> SEQUENCE: 350
acccaactga atggagcggg cggacgaaaa cccttgagca cag                       43

<210> SEQ ID NO 351
<211> LENGTH: 47
<212> TYPE: DNA
<213> ORGANISM: Artificial Sequence
<220> FEATURE:
<223> OTHER INFORMATION: Primer

<400> SEQUENCE: 351
acgcacttga cttgtcttcg ccgggatgcc ttacctagac gcaatga                   47

<210> SEQ ID NO 352
<211> LENGTH: 45
<212> TYPE: DNA
<213> ORGANISM: Artificial Sequence
<220> FEATURE:
<223> OTHER INFORMATION: Primer

<400> SEQUENCE: 352
acccaactga atggagcgcg gcagccgttg aggcaaaagt gatac                     45

<210> SEQ ID NO 353
<211> LENGTH: 48
<212> TYPE: DNA
<213> ORGANISM: Artificial Sequence
<220> FEATURE:
<223> OTHER INFORMATION: Primer

<400> SEQUENCE: 353
acgcacttga cttgtcttcc gagttccgtc cggttaagcg tgacagtc                  48

<210> SEQ ID NO 354
<211> LENGTH: 24
<212> TYPE: DNA
<213> ORGANISM: Artificial Sequence
<220> FEATURE:
<223> OTHER INFORMATION: Primer

<400> SEQUENCE: 354
agaggaggag atagagtagg agat                                            24

<210> SEQ ID NO 355
<211> LENGTH: 25
<212> TYPE: DNA
<213> ORGANISM: Artificial Sequence
<220> FEATURE:
<223> OTHER INFORMATION: Primer

<400> SEQUENCE: 355
taccagccag tatgataaga agaga                                           25

<210> SEQ ID NO 356
<211> LENGTH: 21
<212> TYPE: DNA
<213> ORGANISM: Artificial Sequence
<220> FEATURE:
<223> OTHER INFORMATION: Primer

<400> SEQUENCE: 356
gcacgttgat gacttctgac a                                               21

<210> SEQ ID NO 357
<211> LENGTH: 23
<212> TYPE: DNA
<213> ORGANISM: Artificial Sequence
<220> FEATURE:
<223> OTHER INFORMATION: Primer

<400> SEQUENCE: 357
gcccacaaac aatccaacct tac                                             23

<210> SEQ ID NO 358
<211> LENGTH: 24
<212> TYPE: DNA
<213> ORGANISM: Artificial Sequence
<220> FEATURE:
<223> OTHER INFORMATION: Primer

<400> SEQUENCE: 358
tgcccataac acatttgaca cttt                                            24

<210> SEQ ID NO 359
<211> LENGTH: 20
<212> TYPE: DNA
<213> ORGANISM: Artificial Sequence
<220> FEATURE:
<223> OTHER INFORMATION: Primer

<400> SEQUENCE: 359
ttcggccaca gctaaactcg                                                 20

<210> SEQ ID NO 360
<211> LENGTH: 24
<212> TYPE: DNA
<213> ORGANISM: Artificial Sequence
<220> FEATURE:
<223> OTHER INFORMATION: Primer

<400> SEQUENCE: 360
accttatacg gaacatagca gacg                                            24

```
<210> SEQ ID NO 361
<211> LENGTH: 21
<212> TYPE: DNA
<213> ORGANISM: Artificial Sequence
<220> FEATURE:
<223> OTHER INFORMATION: Primer

<400> SEQUENCE: 361
tcgatgcgct tctatcactt c                                        21

<210> SEQ ID NO 362
<211> LENGTH: 20
<212> TYPE: DNA
<213> ORGANISM: Artificial Sequence
<220> FEATURE:
<223> OTHER INFORMATION: Primer

<400> SEQUENCE: 362
cgccaaatga ctcgcattgt                                          20

<210> SEQ ID NO 363
<211> LENGTH: 22
<212> TYPE: DNA
<213> ORGANISM: Artificial Sequence
<220> FEATURE:
<223> OTHER INFORMATION: Primer

<400> SEQUENCE: 363
gcatgtgcct ttccgaarta aa                                       22

<210> SEQ ID NO 364
<211> LENGTH: 17
<212> TYPE: DNA
<213> ORGANISM: Artificial Sequence
<220> FEATURE:
<223> OTHER INFORMATION: Primer

<400> SEQUENCE: 364
gcgcaacagg gaagcaa                                             17

<210> SEQ ID NO 365
<211> LENGTH: 23
<212> TYPE: DNA
<213> ORGANISM: Artificial Sequence
<220> FEATURE:
<223> OTHER INFORMATION: Primer

<400> SEQUENCE: 365
tgcggatgtc ctatgtctga aag                                      23

<210> SEQ ID NO 366
<211> LENGTH: 22
<212> TYPE: DNA
<213> ORGANISM: Artificial Sequence
<220> FEATURE:
<223> OTHER INFORMATION: Primer

<400> SEQUENCE: 366
catgaccgcc actataacca ga                                       22

<210> SEQ ID NO 367
<211> LENGTH: 22
<212> TYPE: DNA
<213> ORGANISM: Artificial Sequence
<220> FEATURE:
<223> OTHER INFORMATION: Primer
```

<400> SEQUENCE: 367
atgcaacatt agcaggagga tg                                          22

<210> SEQ ID NO 368
<211> LENGTH: 16
<212> TYPE: DNA
<213> ORGANISM: Artificial Sequence
<220> FEATURE:
<223> OTHER INFORMATION: Primer

<400> SEQUENCE: 368
ctggcgctct ccagca                                                 16

<210> SEQ ID NO 369
<211> LENGTH: 25
<212> TYPE: DNA
<213> ORGANISM: Artificial Sequence
<220> FEATURE:
<223> OTHER INFORMATION: Primer

<400> SEQUENCE: 369
ttgcaattag tgtgttaggt ggtaa                                       25

<210> SEQ ID NO 370
<211> LENGTH: 20
<212> TYPE: DNA
<213> ORGANISM: Artificial Sequence
<220> FEATURE:
<223> OTHER INFORMATION: Primer

<400> SEQUENCE: 370
gacaccatgc gttttgcttc                                             20

<210> SEQ ID NO 371
<211> LENGTH: 20
<212> TYPE: DNA
<213> ORGANISM: Artificial Sequence
<220> FEATURE:
<223> OTHER INFORMATION: Primer

<400> SEQUENCE: 371
tcgtaccggc aacaattgac                                             20

<210> SEQ ID NO 372
<211> LENGTH: 20
<212> TYPE: DNA
<213> ORGANISM: Artificial Sequence
<220> FEATURE:
<223> OTHER INFORMATION: Primer

<400> SEQUENCE: 372
gtggcgattt cacgctgtta                                             20

<210> SEQ ID NO 373
<211> LENGTH: 20
<212> TYPE: DNA
<213> ORGANISM: Artificial Sequence
<220> FEATURE:
<223> OTHER INFORMATION: Primer

<400> SEQUENCE: 373
tatccagcac gttccaggtg                                             20

```
<210> SEQ ID NO 374
<211> LENGTH: 20
<212> TYPE: DNA
<213> ORGANISM: Artificial Sequence
<220> FEATURE:
<223> OTHER INFORMATION: Primer

<400> SEQUENCE: 374
aaaaccgcgc cgcgttacct                                              20

<210> SEQ ID NO 375
<211> LENGTH: 20
<212> TYPE: DNA
<213> ORGANISM: Artificial Sequence
<220> FEATURE:
<223> OTHER INFORMATION: Primer

<400> SEQUENCE: 375
ccagaaatcg cgcccgcatt                                              20

<210> SEQ ID NO 376
<211> LENGTH: 20
<212> TYPE: DNA
<213> ORGANISM: Artificial Sequence
<220> FEATURE:
<223> OTHER INFORMATION: Primer

<400> SEQUENCE: 376
tccagcaggt gctggatcgt                                              20

<210> SEQ ID NO 377
<211> LENGTH: 22
<212> TYPE: DNA
<213> ORGANISM: Artificial Sequence
<220> FEATURE:
<223> OTHER INFORMATION: Primer

<400> SEQUENCE: 377
gcgaaatttt tcgccgtact gt                                           22

<210> SEQ ID NO 378
<211> LENGTH: 24
<212> TYPE: DNA
<213> ORGANISM: Artificial Sequence
<220> FEATURE:
<223> OTHER INFORMATION: Primer

<400> SEQUENCE: 378
cattacggca aagtgtgggt caat                                         24

<210> SEQ ID NO 379
<211> LENGTH: 24
<212> TYPE: DNA
<213> ORGANISM: Artificial Sequence
<220> FEATURE:
<223> OTHER INFORMATION: Primer

<400> SEQUENCE: 379
ccatcagcac gttatcgaat cctt                                         24

<210> SEQ ID NO 380
<211> LENGTH: 23
<212> TYPE: DNA
<213> ORGANISM: Artificial Sequence
<220> FEATURE:
<223> OTHER INFORMATION: Primer
```

```
<400> SEQUENCE: 380
cgtatcachg tttgtgtgaa caa                                            23

<210> SEQ ID NO 381
<211> LENGTH: 22
<212> TYPE: DNA
<213> ORGANISM: Artificial Sequence
<220> FEATURE:
<223> OTHER INFORMATION: Primer

<400> SEQUENCE: 381
ggattcacya cttgcaaagt cc                                             22

<210> SEQ ID NO 382
<211> LENGTH: 20
<212> TYPE: DNA
<213> ORGANISM: Artificial Sequence
<220> FEATURE:
<223> OTHER INFORMATION: Prmer

<400> SEQUENCE: 382
ataccgacga cgccgatctg                                                20

<210> SEQ ID NO 383
<211> LENGTH: 20
<212> TYPE: DNA
<213> ORGANISM: Artificial Sequence
<220> FEATURE:
<223> OTHER INFORMATION: Primer

<400> SEQUENCE: 383
ggatcattta tgctggtacg                                                20

<210> SEQ ID NO 384
<211> LENGTH: 20
<212> TYPE: DNA
<213> ORGANISM: Artificial Sequence
<220> FEATURE:
<223> OTHER INFORMATION: Primer

<400> SEQUENCE: 384
ataccgacga cgccgatctg                                                20

<210> SEQ ID NO 385
<211> LENGTH: 20
<212> TYPE: DNA
<213> ORGANISM: Artificial Sequence
<220> FEATURE:
<223> OTHER INFORMATION: Primer

<400> SEQUENCE: 385
tgctattcat tatgcgcagc                                                20

<210> SEQ ID NO 386
<211> LENGTH: 20
<212> TYPE: DNA
<213> ORGANISM: Artificial Sequence
<220> FEATURE:
<223> OTHER INFORMATION: Primer

<400> SEQUENCE: 386
ggcgaaatgg cwgagaacca                                                20
```

```
<210> SEQ ID NO 387
<211> LENGTH: 20
<212> TYPE: DNA
<213> ORGANISM: Artificial Sequence
<220> FEATURE:
<223> OTHER INFORMATION: Primer

<400> SEQUENCE: 387
gagtcttcga agttgtaacc                                                 20

<210> SEQ ID NO 388
<211> LENGTH: 22
<212> TYPE: DNA
<213> ORGANISM: Artificial Sequence
<220> FEATURE:
<223> OTHER INFORMATION: Primer

<400> SEQUENCE: 388
tgaaatatga ctccactcac gg                                              22

<210> SEQ ID NO 389
<211> LENGTH: 24
<212> TYPE: DNA
<213> ORGANISM: Artificial Sequence
<220> FEATURE:
<223> OTHER INFORMATION: Primer

<400> SEQUENCE: 389
cttcagaagc ggctttgatg gctt                                            24

<210> SEQ ID NO 390
<211> LENGTH: 21
<212> TYPE: DNA
<213> ORGANISM: Artificial Sequence
<220> FEATURE:
<223> OTHER INFORMATION: Primer

<400> SEQUENCE: 390
cccaactcgc ttcaggttca g                                               21

<210> SEQ ID NO 391
<211> LENGTH: 20
<212> TYPE: DNA
<213> ORGANISM: Artificial Sequence
<220> FEATURE:
<223> OTHER INFORMATION: Primer

<400> SEQUENCE: 391 ccgttttcc ccagcagcag                                                  20

<210> SEQ ID NO 392
<211> LENGTH: 26
<212> TYPE: DNA
<213> ORGANISM: Artificial Sequence
<220> FEATURE:
<223> OTHER INFORMATION: Primer

<400> SEQUENCE: 392
gagaaaaacc tgcctgtact gctggc                                          26

<210> SEQ ID NO 393
<211> LENGTH: 25
<212> TYPE: DNA
<213> ORGANISM: Artificial Sequence
<220> FEATURE:
<223> OTHER INFORMATION: Primer
```

<400> SEQUENCE: 393
cgcgccacgc tttatagcgg ttaat                                          25

<210> SEQ ID NO 394
<211> LENGTH: 26
<212> TYPE: DNA
<213> ORGANISM: Artificial Sequence
<220> FEATURE:
<223> OTHER INFORMATION: Primer

<400> SEQUENCE: 394
acctaccgca acaccgactt cttcgg                                         26

<210> SEQ ID NO 395
<211> LENGTH: 21
<212> TYPE: DNA
<213> ORGANISM: Artificial Sequence
<220> FEATURE:
<223> OTHER INFORMATION: Primer

<400> SEQUENCE: 395
tgatcagaac tggtaggtga t                                              21

<210> SEQ ID NO 396
<211> LENGTH: 21
<212> TYPE: DNA
<213> ORGANISM: Artificial Sequence
<220> FEATURE:
<223> OTHER INFORMATION: Primer

<400> SEQUENCE: 396
ctcgctgctg gactatattc g                                              21

<210> SEQ ID NO 397
<211> LENGTH: 21
<212> TYPE: DNA
<213> ORGANISM: Artificial Sequence
<220> FEATURE:
<223> OTHER INFORMATION: Primer

<400> SEQUENCE: 397
cgctttcagc tcaagaactt c                                              21

<210> SEQ ID NO 398
<211> LENGTH: 24
<212> TYPE: DNA
<213> ORGANISM: Artificial Sequence
<220> FEATURE:
<223> OTHER INFORMATION: Primer

<400> SEQUENCE: 398
ctttatacct cggtacatca ggtt                                           24

<210> SEQ ID NO 399
<211> LENGTH: 21
<212> TYPE: DNA
<213> ORGANISM: Artificial Sequence
<220> FEATURE:
<223> OTHER INFORMATION: Primer

<400> SEQUENCE: 399
attcgccggc tgrgcrgaga g                                              21

```
<210> SEQ ID NO 400
<211> LENGTH: 17
<212> TYPE: DNA
<213> ORGANISM: Artificial Sequence
<220> FEATURE:
<223> OTHER INFORMATION: Primer

<400> SEQUENCE: 400
atggtggtgc gccagtg                                                  17

<210> SEQ ID NO 401
<211> LENGTH: 18
<212> TYPE: DNA
<213> ORGANISM: Artificial Sequence
<220> FEATURE:
<223> OTHER INFORMATION: Primer

<400> SEQUENCE: 401
gctgaccgag acgttgtc                                                 18

<210> SEQ ID NO 402
<211> LENGTH: 23
<212> TYPE: DNA
<213> ORGANISM: Artificial Sequence
<220> FEATURE:
<223> OTHER INFORMATION: Primer

<400> SEQUENCE: 402
acggcaggcg atttgattta acg                                           23

<210> SEQ ID NO 403
<211> LENGTH: 22
<212> TYPE: DNA
<213> ORGANISM: Artificial Sequence
<220> FEATURE:
<223> OTHER INFORMATION: Primer

<400> SEQUENCE: 403
agctgcgtga tcgagaccta tc                                            22

<210> SEQ ID NO 404
<211> LENGTH: 20
<212> TYPE: DNA
<213> ORGANISM: Artificial Sequence
<220> FEATURE:
<223> OTHER INFORMATION: Primer

<400> SEQUENCE: 404
tcatcatctg cactttccgc                                               20

<210> SEQ ID NO 405
<211> LENGTH: 20
<212> TYPE: DNA
<213> ORGANISM: Artificial Sequence
<220> FEATURE:
<223> OTHER INFORMATION: Primer

<400> SEQUENCE: 405
ccagatcagc gcgaacttca                                               20

<210> SEQ ID NO 406
<211> LENGTH: 20
<212> TYPE: DNA
<213> ORGANISM: Artificial Sequence
<220> FEATURE:
<223> OTHER INFORMATION: Primer
```

<400> SEQUENCE: 406
tcacaggtcg ccagcgcttc                                                 20

<210> SEQ ID NO 407
<211> LENGTH: 20
<212> TYPE: DNA
<213> ORGANISM: Artificial Sequence
<220> FEATURE:
<223> OTHER INFORMATION: Primer

<400> SEQUENCE: 407
tcccggcaga taagctgtgg                                                 20

<210> SEQ ID NO 408
<211> LENGTH: 20
<212> TYPE: DNA
<213> ORGANISM: Artificial Sequence
<220> FEATURE:
<223> OTHER INFORMATION: Primer

<400> SEQUENCE: 408
tcggcgacac ggatgacggc                                                 20

<210> SEQ ID NO 409
<211> LENGTH: 20
<212> TYPE: DNA
<213> ORGANISM: Artificial Sequence
<220> FEATURE:
<223> OTHER INFORMATION: Primer

<400> SEQUENCE: 409
gtccatgtag gcgttcaggg                                                 20

<210> SEQ ID NO 410
<211> LENGTH: 29
<212> TYPE: DNA
<213> ORGANISM: Artificial Sequence
<220> FEATURE:
<223> OTHER INFORMATION: Primer

<400> SEQUENCE: 410
atggaaagta aagtagttgt tccggcaca                                       29

<210> SEQ ID NO 411
<211> LENGTH: 19
<212> TYPE: DNA
<213> ORGANISM: Artificial Sequence
<220> FEATURE:
<223> OTHER INFORMATION: Primer

<400> SEQUENCE: 411
ggacgcagca ggatctgtt                                                  19

<210> SEQ ID NO 412
<211> LENGTH: 20
<212> TYPE: DNA
<213> ORGANISM: Artificial Sequence
<220> FEATURE:
<223> OTHER INFORMATION: Primer

<400> SEQUENCE: 412
agcgcgttct gttcaaatgc                                                 20

```
<210> SEQ ID NO 413
<211> LENGTH: 21
<212> TYPE: DNA
<213> ORGANISM: Artificial Sequence
<220> FEATURE:
<223> OTHER INFORMATION: Primer

<400> SEQUENCE: 413
caggttcaga actctctctg t                                              21

<210> SEQ ID NO 414
<211> LENGTH: 20
<212> TYPE: DNA
<213> ORGANISM: Artificial Sequence
<220> FEATURE:
<223> OTHER INFORMATION: Primer

<400> SEQUENCE: 414
tcggtaacgg tgttgtgctg                                                20

<210> SEQ ID NO 415
<211> LENGTH: 20
<212> TYPE: DNA
<213> ORGANISM: Artificial Sequence
<220> FEATURE:
<223> OTHER INFORMATION: Primer

<400> SEQUENCE: 415
catacggtaa gccacgcaga                                                20

<210> SEQ ID NO 416
<211> LENGTH: 20
<212> TYPE: DNA
<213> ORGANISM: Artificial Sequence
<220> FEATURE:
<223> OTHER INFORMATION: Primer

<400> SEQUENCE: 416
acctttgtag ctgtaccacg                                                20

<210> SEQ ID NO 417
<211> LENGTH: 21
<212> TYPE: DNA
<213> ORGANISM: Artificial Sequence
<220> FEATURE:
<223> OTHER INFORMATION: Primer

<400> SEQUENCE: 417
agcgtgaagg taaaacctgt g                                              21

<210> SEQ ID NO 418
<211> LENGTH: 23
<212> TYPE: DNA
<213> ORGANISM: Artificial Sequence
<220> FEATURE:
<223> OTHER INFORMATION: Primer

<400> SEQUENCE: 418
ttgattcacc agcgcgtatt gtc                                            23

<210> SEQ ID NO 419
<211> LENGTH: 21
<212> TYPE: DNA
<213> ORGANISM: Artificial Sequence
<220> FEATURE:
<223> OTHER INFORMATION: Primer
```

<400> SEQUENCE: 419
aggtatctgc ttcaatcagc g  21

<210> SEQ ID NO 420
<211> LENGTH: 23
<212> TYPE: DNA
<213> ORGANISM: Artificial Sequence
<220> FEATURE:
<223> OTHER INFORMATION: Primer

<400> SEQUENCE: 420
atcggaaatc ctatttcaca ttc  23

<210> SEQ ID NO 421
<211> LENGTH: 23
<212> TYPE: DNA
<213> ORGANISM: Artificial Sequence
<220> FEATURE:
<223> OTHER INFORMATION: Primer

<400> SEQUENCE: 421
ggtgttgtat taataacgat atc  23

<210> SEQ ID NO 422
<211> LENGTH: 22
<212> TYPE: DNA
<213> ORGANISM: Artificial Sequence
<220> FEATURE:
<223> OTHER INFORMATION: Primer

<400> SEQUENCE: 422
ctaggaactg caatcttaat cc  22

<210> SEQ ID NO 423
<211> LENGTH: 23
<212> TYPE: DNA
<213> ORGANISM: Artificial Sequence
<220> FEATURE:
<223> OTHER INFORMATION: Primer

<400> SEQUENCE: 423
tggtaaaatc gcatgtccaa ttc  23

<210> SEQ ID NO 424
<211> LENGTH: 20
<212> TYPE: DNA
<213> ORGANISM: Artificial Sequence
<220> FEATURE:
<223> OTHER INFORMATION: Primer

<400> SEQUENCE: 424
atcgttttat cgggaccatc  20

<210> SEQ ID NO 425
<211> LENGTH: 23
<212> TYPE: DNA
<213> ORGANISM: Artificial Sequence
<220> FEATURE:
<223> OTHER INFORMATION: Primer

<400> SEQUENCE: 425
tcattaacta caacgtaatc gta  23

```
<210> SEQ ID NO 426
<211> LENGTH: 23
<212> TYPE: DNA
<213> ORGANISM: Artificial Sequence
<220> FEATURE:
<223> OTHER INFORMATION: Primer

<400> SEQUENCE: 426
gttaaaatcg tattacctga agg                                          23

<210> SEQ ID NO 427
<211> LENGTH: 23
<212> TYPE: DNA
<213> ORGANISM: Artificial Sequence
<220> FEATURE:
<223> OTHER INFORMATION: Primer

<400> SEQUENCE: 427
gacccttttg ttgaaaagct taa                                          23

<210> SEQ ID NO 428
<211> LENGTH: 23
<212> TYPE: DNA
<213> ORGANISM: Artificial Sequence
<220> FEATURE:
<223> OTHER INFORMATION: Primer

<400> SEQUENCE: 428
tcgttcattc tgaacgtcgt gaa                                          23

<210> SEQ ID NO 429
<211> LENGTH: 23
<212> TYPE: DNA
<213> ORGANISM: Artificial Sequence
<220> FEATURE:
<223> OTHER INFORMATION: Primer

<400> SEQUENCE: 429
tttgcacctt ctaacaattg tac                                          23

<210> SEQ ID NO 430
<211> LENGTH: 23
<212> TYPE: DNA
<213> ORGANISM: Artificial Sequence
<220> FEATURE:
<223> OTHER INFORMATION: Primer

<400> SEQUENCE: 430
cagcatacag gacacctatt ggc                                          23

<210> SEQ ID NO 431
<211> LENGTH: 23
<212> TYPE: DNA
<213> ORGANISM: Artificial Sequence
<220> FEATURE:
<223> OTHER INFORMATION: Primer

<400> SEQUENCE: 431
cgttgaggaa tcgatactgg aac                                          23
```

SYSTEMS AND METHODS OF DIAGNOSING AND CHARACTERIZING INFECTIONS

CROSS REFERENCE TO RELATED APPLICATIONS

This application is the U.S. National Stage of International Application No. PCT/US2016/060369, filed on Nov. 3, 2016, which claims priority to and the benefit of U.S. Provisional Application Ser. No. 62/250,565, filed on Nov. 4, 2015, the contents of each of which are hereby incorporated by reference in their entireties.

STATEMENT REGARDING FEDERALLY SPONSORED RESEARCH OR DEVELOPMENT

This invention was made with governmental support under award number R01AI090782 awarded by the National Institutes of Health (NIH). The United States government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 77,824 byte ASCII (text) file named "91482_196_Sequence_Listing" created on Oct. 29, 2016.

FIELD OF INVENTION

The present invention is generally related to systems and methods of sequencing biological molecules for determinations regarding the presence and/or absence of infectious agents, and particularly related to systems and methods for the diagnosis of infections and determination of the presence of antimicrobial-resistance markers using nucleic-acid sequencing (e.g., amplicon-based sequencing).

BACKGROUND OF THE INVENTION

Once highly treatable, common bacterial infections are becoming increasingly more difficult to characterize and manage. Gram-negative infections, including *Klebsiella pneumoniae, Acinetobacter baumannii, Pseudomonas aeruginosa, Enterobacter* species and *Escherichia coli* and Gram-positive infections, including *Staphylococcus aureus*, are all considered high-priority target pathogens for which new therapeutics are urgently needed. These are the components of the widely recognized ESKAPE pathogens, which have become a focal point for the development of new antibiotics. The lack of new drugs makes it critical that clinicians receive rapid and informative data on their patients' infections and their likely response to therapy. This clinical and public health crisis is coming at a time when we have greater scientific understanding of the mechanisms of resistance and better access to molecular technology to detect and characterize those mechanisms than ever before; however, the barriers between genomic research and the clinical lab also remains large and therefore the separation between genotype and phenotype remains largely un-bridged.

Some of these ESKAPE pathogens (e.g., *K. pneumoniae, A. baumannii, P. aeruginosa, Enterobacter* spp. and ExPEC *E. coli*) are all widely distributed Gram-negative bacteria demonstrating high levels of multi-drug resistance, including resistance to carbapenems and other last-line drugs. While similar in many respects, including all being primary causes of healthcare-associated infections (HAI), individually, these organisms present many unique problems to clinical medicine and public health. *P. aeruginosa* is a major cause of pneumonia in cystic fibrosis patients and outbreaks in neonatal intensive care units, and is frequently shown to colonize water networks in hospitals. Its high rates of intrinsic resistance frequently confound clinical susceptibility testing. *A. baumannii* is responsible for up to 80% of all intensive care unit (ICU) bloodstream infections; its high-rate of transmission in the healthcare setting can be attributed to high desiccation tolerance, enabling it to survive for long periods on fomites. Extra-intestinal Pathogenic *E. coli* (ExPEC) has become a global cause of antimicrobial resistance (AR) bacteremia and urinary tract infections, particularly specific strains, such as the well-studied ST131 strain. *Enterobacter* has been seen to have comparable prevalence of ESBLs and other plasmid-mediated resistance as *Klebsiella* and *E. coli*. In addition, at least some of the aforementioned pathogens have developed resistance to multiple antibiotics typically through several different mechanisms. The mechanisms for resistance are variable, can occur in combinations and in some cases are synergistic.

The rapid depletion of available antibiotics combined with an even more rapid increase in bacterial mechanisms of multi-drug resistance is a call to action for molecular researchers, medical and public health officials and the biomedical industry to join forces to develop and translate more informative diagnostic tools for the clinician, to better characterize and respond to AR in bacterial infections. While bacterial culturing may remain the gold standard for diagnosis and characterizing resistance, standard culturing processes are time consuming, potentially hazardous, and require specific microbiological skills and facilities.

In addition, antibiotic susceptibility analysis techniques may vary for different species, as there is no single approach that can be used to rapidly diagnose and characterize infections with all target agents. Clearly a new approach is required—the detection of established and emerging multi-drug resistant bacteria directly from clinical specimens demands a sensitive and comprehensive diagnostic approach that is capable of rapidly identifying trace amounts of genotypic targets in human samples and using that information to develop phenotypic profiles. The scientific and clinical research community now has more knowledge and cutting edge technology than ever before, allowing them to address this health crisis with such an approach.

Given these public-health issues, there is a demonstrated need to develop a novel, multiplexed, targeted sequence analysis system for the detection and characterization of AR markers in critical ESKAPE bacteria, typically associated with HAIs, directly from clinical samples. As described herein, the inventors have developed an approach that is capable of identifying all known classes of AR mechanisms, including mutations, SNPs, mobile elements, gene amplification, and expression modulation.

DETAILED DESCRIPTION

As used herein, the verb "comprise" as is used in this description and in the claims and its conjugations are used in its non-limiting sense to mean that items following the word are included, but items not specifically mentioned are not excluded. Plural encompasses singular and vice versa;

e.g., the singular forms "a," "an," and "the" include plural referents unless expressly and unequivocally limited to one referent.

Some embodiments of the invention provide systems and methods for diagnosing and/or identifying infectious organisms and thereafter making one or more genotypic determinations. Moreover, in addition to the diagnostic and genotypic capabilities of the instant invention, some embodiments may also provide methodologies of making genetic/typing determinations of the infectious organisms to provide those of ordinary skill in the art with epidemiological information about the infectious organisms (e.g., strain type). In addition, some embodiments of the invention can be employed with samples that do not require isolation and culturing of the infectious organisms (i.e., embodiments include the capability to directly analyze samples from a patient).

Some embodiments of the invention may provide methods of (i) diagnosing and/or identifying an infectious organism; (ii) determining the presence of one or more antibiotic resistance targets of the infectious organism; and/or (iii) determining a strain identity of the infectious organism. In some aspects, these three steps of some embodiments of the invention may be performed substantially or completely simultaneously, or, in other aspects, may be performed sequentially (e.g., in any sequence). Moreover, in some embodiments, one or more of these three steps may be omitted. For example, in some embodiments, the first two steps may be performed according to some aspects of the invention and the user may omit the third step in the event that the user does not desire strain information about the infectious organism. In other embodiments, one or more of the first and/or second steps recited above may be omitted.

With respect to the three steps/methodologies, some or all of these steps may include an analysis of one or more markers at each step. For example, pre-selected markers can be used to make determinations regarding the presence and/or absence of one or more infectious microorganisms (e.g., ESKAPE pathogens). In particular, a series of pre-selected markers may be chosen to provide relevant differential information regarding the identification. For example, makers can be selected that are specific for a plurality of potentially pathogenic microorganisms so that presence or absence of certain markers provides highly specific relevant information. Moreover, the same and/or different pre-selected markers can be used to make predictions about a phenotype of the infectious microorganisms. In some embodiments, as described in greater detail below, the phenotypic predictions can be generally or specifically directed to determining the presence of one or more AR markers. In addition, some of the same and/or different pre-selected markers as recited above can be used to provide users with information regarding a strain identity of the infectious microorganism.

As described in greater detail herein, some embodiments of the invention may include amplicon-based sequencing of the one or more markers to make the aforementioned determinations. Some embodiments of the invention include systems and methods of preparing samples for one or more downstream processes that can be used for assessing one or more markers for any of the previously mentioned purposes. Some embodiments of the invention may comprise a universal indexing sequencing strategy for use in downstream sequencing platform processes. By way of example only, some embodiments of the invention comprise a universal indexing sequencing strategy that can be used to amplify multiple genomic regions (e.g., markers, as described below) from a DNA sample simultaneously in a single reaction for the sequencing of one or more amplicons. One or more embodiments of the invention can be used with any desired sequencing platform, such as the ILLUMINA® Next Generation Sequencing (e.g., MiSEQ) platform, Life Technologies' Ion Torrent System, or any other sequencing system now known or developed in the future.

Some embodiments may be configured to enable relatively simple, rapid (e.g., microorganism-culture independent), inexpensive, and efficient preparation of samples for use on, in, and/or with downstream sequencing platforms. For example, some embodiments may use a sequence coupled to one or more oligonucleotides/primers (as used herein, oligonucleotides and primers are used interchangeably). More specifically, one or more amplicons per sample can be generated using a hybrid oligonucleotide that is designed for amplification of a marker and incorporation of at least one universal tail sequence into the resulting amplicon. As a result, additional steps that may be conventionally required to prepare samples for sequencing can be limited or removed entirely. Further information regarding the universal tail, amplicon-based sequencing strategy can be found in PCT/US2014/064890, which is hereby incorporated by reference in its entirety for all purposes.

In some embodiments, the methodology may include performing downstream sequencing on one or more amplicons. For example, in order to minimize and/or eliminate the need for cultures of microorganisms or large inputs of nucleic acids, methodologies of the instant invention may include an initial PCR step to create amplicons that correspond to the one or more pre-selected markers. As such, some embodiments require only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of some conventional systems.

Some embodiments of the invention can be used for and/or in complement with high-throughput amplicon sequencing of markers, which can be very useful for a variety of molecular genetic genotyping/predicted-phenotyping applications, including clinical sample analysis. For example, use of the systems and methods of the invention can be employed with sequencing platforms to provide rapid, high-yield sequence data, which can enable the sequencing of multiple markers/amplicons from many samples in a relatively short period of time. Specifically, in some embodiments, amplicons can be selected and PCR reactions can be designed to provide information that can be used to make clinically relevant determinations after sequencing of the amplicons.

Overall, embodiments of the invention may generally include systems and methods that provide multiplexed marker/sequence amplification, sequencing, and analysis for the identification/detection and characterization of AR markers in critical ESKAPE pathogens and HAI-related pathogens from culture-independent samples. In other words, embodiments of the invention provide diagnostic methodologies with the ability to provide phenotypic and predicted-genotypic information without the need for separately culturing a sample from a subject. In conventional diagnostic procedures, the need for culturing can add time and complexity, which is avoided by the instantly recited invention.

In some preferred aspects, the methodology may include creating a series of oligonucleotides designed to provide multiplexed amplification of one or more markers to produce the desired amplicons. In particular, the one or more markers and amplicons thereof can be selected/amplified to provide users with clinically relevant information related to identification of one or more potentially infectious microorganisms and phenotypic and genotypic information about the microorganisms (e.g., AR status and strain identity). After production of the amplicons (e.g., via PCR amplification), which may include the universal tail sequences, as detailed above and below, the method may include processing the resulting amplicons for downstream sequencing and thereafter sequencing the processed amplicons. After processing and analysis of the resulting sequencing data, one of skill in the art can make any necessary determinations regarding the identification of one or more microorganisms that may have been contained within the sample and predicted-phenotypic and/or genotypic information revealed.

Generally, some embodiments of the present invention can be used to detect, identify, assess, sequence, or otherwise evaluate a marker. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection, identification, assessment, sequencing, or any other evaluation of the marker may encompass an assessment of a change in copy number (e.g., copy number of a gene or other forms of nucleic acid) or in the detection of one or more translocations. Moreover, in some embodiments, the marker may be relevant to a particular phenotype or genotype. By way of example only, in some embodiments, the marker may be related to phenotypes including antibiotic resistance, virulence, or any other phenotype.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

In some aspects, the markers may include one or more sets of amplifiable nucleic acids that can provide diagnostic information about the microorganisms. For example, the markers may include amplifiable nucleic acid sequences that can be used to assess the presence and/or absence of one or more microorganism that may have the potential to cause a diseased state in the subject. In some embodiments, the markers may include amplifiable nucleic acid sequences that can be used to identify one or more of the following exemplary microorganisms: *Klebsiella pneumoniae, Serratia marcescens, Proteus mirabilis, Providencia alcalifaciens, Providencia stuartii, Enterococcus faecalis, Enterococcus faecium, Klebsiella oxytoca, Pseudomonas aeruginosa, Staphylococcus aureus, Escherichia coli, Acinetobacter baumanii, Acinetobacter calcoaceticus* (including the Acb complex), *Streptococcus pneumoniae, Streptococcus agalactiae, Enterobacter cloacal, Enterobacter aerogenes, Streptococcus pyogenes, Streptococcus dysgalactia,* and *Streptococcus equi*. In some embodiments, the methods may include the use of one or more than one marker per microorganism. Moreover, in some embodiments, one or more of the microorganisms may not be considered pathogenic to certain subjects, but the methodology employed herein can still rely on detection of pathogenic and nonpathogenic microorganisms for differential diagnoses/diagnostics. In some embodiments, the oligonucleotides (with or without the universal tail sequences detailed herein) listed in Table 1 can be used with embodiments of the invention to amplify one or more markers from the microorganisms to provide diagnostic/identification information to the user.

Moreover, in some embodiments, one or more the markers associated with the plurality of microorganisms can be amplified in a multiplex manner. For example, in some aspects, nucleic acids can be obtained from the sample and the oligonudeotides used to amplify one or more of the markers used to identify/diagnose can be added to a single mixture to produce a plurality of amplicons in a single reaction mixture. In other aspects, the oligonudeotides can be added to multiple mixtures to provide for the creation of multiple amplicons in multiple mixtures.

In some aspects, the markers may include one or more sets of amplifiable nucleic acids that can provide characterization information about the microorganisms. For example, the markers may include amplifiable nucleic acid sequences that can be used to assess the presence and/or absence of one or more antibiotic resistance (AR) mechanisms within the microorganisms. In some embodiments, the markers may include amplifiable nucleic acid sequences that can be used to identify the presence of one or more of the following AR markers: $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2''), vat, vga, ermA, ermB, ermC, mecA, int, sul, mecA, aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_iii, bl2a_kcc, bl2a_nps, bl2a_okp, bl2a_pc, bl2be_ctxm, bl2be_oxy1, bl2be_per, bl2be_shv2, bl2b_rob, bl2b_tem1, bl2b_tem2, bl2b_tem, bl2b_tle, bl2b_ula, bl2c_bro, bl2c_pse1, bl2c_pse3, bl2d_lcr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_sme1, bl2_ges, bl2_kpc, bl2_len, bl2_veb, bl3_ccra, bl3_cit, bl3_cpha, bl3_gim, bl3_imp, bl3_1, bl3_shw, bl3_sim, bl3_vim, ble, bit, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdti, mdtm, mdtn, mdto, mdtp, meca, mecrl, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, text, tety, tetz, tirc, tmrb, tolc, tsnr, vana, vanb, vanc, vand, vane, vang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd.

In some specific embodiments of the methodology, the method may include an analysis of the following AR markers: blaKPC (beta lactam resistance), blaNDM (beta lactam resistance), rmtA (aminoglycoside resistance), rmtB (aminoglycoside resistance), rmtC (aminoglycoside resistance), rmtD1 and rmtD2 (aminoglycoside resistance), npmA (aminoglycoside resistance), armA (aminoglycoside resistance), gyrA (fluoroquinolone resistance), parC (fluoroquinolone resistance), qnrA (fluoroquinolone resistance), qnrC (fluoroquinolone resistance), qnrD (fluoroquinolone resistance), qnrS (fluoroquinolone resistance), qnrB (fluoroquinolone resistance), blaCTX-M (beta lactam resistance), dfrA markers (dihydrofolate reductase production affecting resistance to trimethoprim), dfrB markers (dihydrofolate reductase production affecting resistance to trimethoprim), sul markers (dihydropteroate synthase production affecting resistance to sulfonamides) *Staphylococcus* rpoB (vancomycin intermediate resistance), and known *Staphylococcus* AR markers, including linA, mecA, vanA, aacA, blaZ, ermA, ermC, tetK, tetM, and msrA. In some embodiments, the oligonucleotides (with or without the universal tail sequences detailed herein) listed in Table 2 can be used with embodiments of the invention to amplify one or more markers from the microorganisms to provide AR information to the user.

Moreover, in some embodiments, one or more the AR markers associated can be amplified in a multiplex manner. For example, in some aspects, nucleic acids can be obtained from the sample and the oligonucleotides used to amplify one or more of the AR markers used to identify/characterize the AR potential of the microorganisms can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the AR markers and the markers used to identify microorganisms/diagnose an infection can also occur in a multiplex manner such that some or all of the amplicons are generated in a single reaction for a particular sample. In other aspects, amplification of the AR markers and the markers used to identify microorganisms/diagnose an infection can occur in multiple reaction vessels.

In some aspects, the markers may include one or more sets of amplifiable nucleic acids that can provide strain identity information about the microorganisms. For example, the markers may include amplifiable nucleic acid sequences that can be used to assess the presence and/or absence of specific strains of microorganisms. In some embodiments, the markers may include amplifiable nucleic acid sequences that can be used to identify the presence of one or more of the following strains of microorganisms: methicillin-resistant *Staphylococcus aureus* (orfX junction), methicillin-resistant *Staphylococcus epidermidis* (orfX junction or cfr), *S. aureus* strain USA300, *S. aureus* strain CC8, *S. aureus* strain USA300/500, *S. aureus* strain Archaic Iberian, *S. aureus* strain True Iberian, *S. aureus* strain ST239, *S. aureus* strain CC5, *Staphylococcus* strains comprising the tuf gene, SCCmec typing, including the following *S. aureus* strains, ccrB2, mecl, IS1272J, ccrC, ccrB1, ccrB3, ccrB4, mecC2, SCCmecIVa-J1, and sccmecIVa. The strain identification markers may also include further *S. aureus* typing markers MRSA sea and MRSA seb and *E. coli* pathovar typing, including the following markers: Shiga toxin genes, *E. coli* aggR, T3SS, *E. coli* virulence markers, *E. coli* and *Shigella* invasion antigen, *E. coli* enterotoxin, *E. coli* UPEC, *E. coli* H30-Rx, trpA, pabB, uidA, rfbO16, and rfbO25b. In some aspects, the strain identification markers may further include markers for strain identification of *K. pneumoniae* strains, including ST258-strain specific SNP 3576137-Y, rpoB, gapA, mdh, phosphoglucose isomerase, phoE, infB, and tonB. The markers for strain identification may also include the CG258 ID assay, a marker for *Klebsiella* capsule type (wzi gene of cps locus), markers for *E. coli* strain identification (adk, fumC, gyrB, icd, mdh, purA, and recA), markers for *S. aureus* strain identification (arc, aro, glp, gmk, pta, tpi, and yqi), and markers for *Streptococcus pyogenes* identification. Moreover, in some embodiments, one or more control nucleotide sequences can be added to any reactions to ensure proper amplification. In some embodiments, the oligonucleotides (with or without the universal tail sequences detailed herein) listed in Table 3 can be used with embodiments of the invention to amplify one or more markers from the microorganisms to provide AR information to the user. In other embodiments, the oligonucleotides (with or without the universal tail sequences detailed herein) listed in Table 9 can be used with embodiments of the invention to amplify one or more markers from the microorganisms to provide lineage identification information to the user.

Moreover, in some embodiments, one or more the strain identification markers associated can be amplified in a multiplex manner. For example, in some aspects, nucleic acids can be obtained from the sample and the oligonucleotides used to amplify one or more of the strain identification markers used to identify the strain of the microorganisms can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the strain identification markers, the AR markers, and/or the markers used to identify microorganisms/diagnose an infection can also occur in a multiplex manner such that some or all of the amplicons are generated in a single reaction for a particular sample. In other aspects, amplification of the strain identification markers, the AR markers, and/or the markers used to identify microorganisms/diagnose an infection can occur in multiple reaction vessels. Overall, as described in greater detail below, regardless of the multiplex nature of some embodiments of the invention, after amplification of the markers detailed above, the method may include processing and sequencing the resulting amplicons to provide information related to the identification, characterization, and strain identity of one or more microorganisms that may be present within the sample.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one marker-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

The algorithm for Ct values in real time-PCR calculates the cycle at which each PCR amplification reaches a significant threshold. The calculated Ct value is proportional to the number of marker copies present in the sample, and the Ct value is a precise quantitative measurement of the copies of the marker found in any sample. In other words, Ct values represent the presence of respective marker that the primer sets are designed to recognize. If the marker is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. In some embodiments, sample may comprise a portion of a non-animal organism, such as a plant (e.g., castor beans or derivatives thereof).

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and bacteria).

With respect to use of the sample or biological sample, embodiments of the claimed methodology provide improvements compared to conventional methodologies. Specifically, conventional methodologies of identifying and characterizing microorganisms include the need for morphological identification and culture growth. As such, conventional methodologies may take an extended period of time to identify the microorganism and may then require further time to identify whether the microorganism possesses and AR markers. Some embodiments of the invention can provide a user with information about any microorganisms present in a sample without the need for additional culturing because of the reliance of nucleic acid amplification and sequencing. In other words, direct extraction of nucleic acids coupled with amplification of the desired markers and downstream sequencing can reduce significantly the time required to obtain diagnostic, AR, and strain identifying information.

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfuryrlase enzyme converts pyrophosphate into ATP that in turn catalyzes the conversion of luciferin to oxyluciferin which results in the generation of visible light that is then detected by a camera or other sensor capable of capturing visible light.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Nucleic acid sequences may be identified by the IUAPC letter code which is as follows: A—Adenine base; C—Cytosine base; G—guanine base; T or U—thymine or uracil base. M—A or C; R—A or G; W—A or T; S—C or G; Y—C or T; K—G or T; V—A or C or G; H—A or C or T; D—A or G or T; B—C or G or T; N or X—A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, as previously mentioned, the method may include the use of massively parallel sequencing, as detailed in U.S. Pat. Nos. 8,431,348 and 7,754,429, which are hereby incorporated by reference in their entirety.

Some embodiments of the invention comprise multiple steps and/or processes that are carried out to execute the universal tail indexing strategy to prepare amplicons corresponding to desired markers for sequencing. In some embodiments, one or more makers for a given sample or template can be selected, as described above. Some embodiments of the invention can be used in conjunction with an analysis of one or more markers (e.g., genes/alleles) associated with a particular phenotype (e.g., resistance to one or more pharmaceuticals, such as antibiotics). By way of example only, some embodiments of the invention can be used to detect and/or quantify the development of antibiotic resistance in populations of patients infected with an organism. As such, in some aspects, prior to performing additional steps, an investigator can assess the markers present within the genome of the organism to determine which markers are implicated in the development of antibiotic resistance. For example, markers can be selected that may contain a SNP or other change or alteration that can confer at least partial antibiotic resistance. In other aspects of the invention, markers can be selected that are not implicated in antibiotic resistance, but are associated with other phenotypes/genotypes that are desirable for further analysis.

After selection of the markers, marker-specific primers/ oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 100 bp, 150 bp, 200 bp, 250 bp, 300 bp, 350 bp, 400 bp, 450 bp, 500 bp, 1,000 bp, or any size amplicon greater in size or therebetween.

As previously mentioned, some embodiments of the invention may include a multiplex PCR reaction. For example, marker-specific primers can be designed for multiple markers or multiple regions of the same marker such that multiple amplicons of between about 50 bp and 1,000 bp are being produced within a single PCR reaction vessel. In other words, the forward and reverse primers can be designed to function within a given set of temperature parameters such that more than one amplicon can be successfully amplified from a given template within a single PCR reaction mixture. As such, multiple amplicons can be prepared using the universal tail indexing strategy for sequencing preparation.

In some embodiments, the forward and reverse primers that have been designed for each of the markers can be modified to include a universal tail. For example, the universal tail sequences can be relatively or completely unique sequences of nucleotides that are coupled to the 5' ends of some or all of the forward and reverse marker-specific primers. In some aspects, the universal tail sequences can be selected such that there is little to no overlap in sequence between portions of the markers that are being amplified and the universal tail sequences. Moreover, the universal tail sequences can comprise a length between ten and twenty nucleotides in length. In some embodiments, the universal tail sequences can be any other length, as desired by the user to meet the needs and requirements of the reaction. As such, the universal tail sequences can exhibit a relatively negligible impact on binding of the forward and reverse marker-specific primers to the template sequence to enable amplification. Moreover, as a result of being included on the 5' end of the forward and reverse marker-specific primers, the universal tail sequences will form a portion of the resulting amplicons. In addition, in some aspects of the invention, the sequences selected for the universal tail sequences can be at least partially correlated with the chemical composition of the template nucleic acids. For example, in some aspects, the sequences selected for the universal tail sequences can be at least partially correlated with the G-C content of the organism from which the template is isolated.

In some aspects, some or all of the universal tail sequences can be at least partially unique. In some embodiments, each of the 5' ends of all of the forward marker-specific primers within a given PCR assay mixture can comprise the same or a similar universal tail sequence (e.g., a first universal tail sequence or UT1). Similarly, each of the 5' ends of all of the reverse marker-specific primers within the same PCR assay mixture can comprise a second universal tail sequence (UT2) that differs from the first universal tail sequence. As such, each respective sample from which a template sequence is used in the multiplex PCR assay will have two unique universal tail sequences. Accordingly, each forward and reverse marker-specific primer within a multiplex PCR mixture will include a unique universal tail sequence. For example, if the PCR includes 35 different samples, 35 universal tail sequences can be employed for the forward primers in each of the 35 unique reactions (i.e., not including technical replicates) and 35 universal tail sequences can be employed for the reverse primers in each of the 35 unique reactions (i.e., not including technical replicates). Overall, the forward and reverse marker-specific primers that each comprise the universal tail sequences can comprise a generally short length (e.g., 25-50 bp), which can facilitate simultaneous amplification of multiple targets in a single reaction.

In addition, some embodiments of the invention may comprise performing quantitative PCR to optimize the multiplex PCR assay. For example, after design of the forward and reverse marker-specific primers that each include a universal tail sequence, the contemplated multiplex PCR assays can be performed using quantitative PCR (e.g., using DNA as a template) to assess relative quantities of the amplicons produced. Accordingly, the sequence coverage of each amplicon is considered to be equal if the quantities of the amplicons produced by the multiplex quantitative PCR appear to be equal. If the quantities of the amplicons produced by the multiplex quantitative PCR do not appear to be equal, the forward and/or reverse marker-specific primers can be altered and re-optimized until adequate quantities of amplicons are produced.

After design and adequate optimization of the multiplex PCR assay comprising multiple forward and reverse marker-specific primers that each include universal tail sequences, the multiplex PCR can be performed to obtain the amplicons associated with the above-described markers. In some embodiments, template that has been previously isolated from a sample can be used for the amplification of the amplicons. In some aspects, multiple PCR reaction replicates can be performed for each sample template and one or more control templates.

In some embodiments, after successful production of the amplicons during the multiplex PCR assay, the resulting amplicons can be further processed to provide sequencing-ready amplicons. For example, some embodiments of the invention may comprise an indexing extension step. In some aspects, the indexing extension step may comprise extending the optimized multiplex amplicons using a set of indexing and common primers that recognize the respective universal tail sequences used for the particular group of amplicons in a minimal cycle PCR assay (e.g., 5-10 total cycles). In particular, each multiplex set of amplicons to be sequenced can be extended with a different set of index oligonucleotides and common oligonucleotides that recognize UT1 and UT2, respectively. In some aspects, the index sequence of the index oligonucleotides can be custom designed to allow for the selection of an index sequence from potentially thousands of different index sequences.

After this step, the resulting products include a set of amplicons for each sample/template that comprise the same index and any necessary sequences that may be required for a particular sequencing platform (e.g., platform sequences associated with the ILLUMINA® Next Generation sequencing platform). Thereafter, the resulting extension-reaction products can be quantified, pooled, and sequenced using a desired platform. In some aspects, the inclusion of the universal tail sequences on the index and common primers can coincide with the use of genomic and index read primers in the mixture of sequencing primer reagents. For example, some embodiments of the invention are capable of pooling multiple amplicons with multiple indices in a single sequencing run to provide 40,000×-95,000× coverage across the amplicons. In other embodiments, the systems and methods associated with the invention can be configured to provide any level of sequencing coverage that is desirable to the user (e.g., higher or lower that the coverage levels discussed above). In some embodiments, after sequencing and generation of the sequence data, the resulting data can be demultiplexed and the sequence files can be aligned to the appropriate references sequences for subsequent sequence analyses.

Embodiments of the invention offer additional advantages relative to conventional systems. For example, some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems. Moreover, the inclusion of non-desirable template materials can also interfere in one or more downstream processes in conventional systems and methods. For example, if an investigation is being conducted that focuses on one or more organisms that may be associated with another organism (e.g., bacteria associated with a human); the sampling of the target organism may result in template contamination from the host organism.

In particular, in some aspects, obtaining samples of pathogenic or commensal bacteria from, on, or within a human may also result in the collection of human tissue. As such, when isolating the template, human nucleic acids may contaminate the bacterial template. Some embodiments of the invention are configured such that the contaminating template (e.g., from a human) would not interfere with downstream processes, including sequencing. For example, some embodiments of the invention operate such that only a limited amount of starting template (e.g., 500 femtograms or greater) can be used. Moreover, some embodiments are also configured such that the starting material (e.g., template contaminated with foreign nucleic acids) can still produce the required amplicons for sequencing in the presence of more than a 1,000-fold excess of contaminating template with no discernible inhibition of the multiplex PCR.

In certain aspects, the present invention provides an assay that works with as little as about 1pg, about 900fg, about 800fg, about 700fg, about 600fg, about 500fg, about 400fg, about 300fg, about 200fg, or about 100fg of genomic DNA.

EXAMPLES

The inventors employed embodiments of the methods detailed herein to assess the presence of microorganisms in control samples from respiratory, wound, nasal swab, and urine specimens using oligonucleotides/primers detailed in Tables 1 and 2 to amplify desired markers. Thereafter, the resulting amplicons were sequenced using next-generation sequencing technology to obtain information on the identity and AR characteristics of the microorganisms in the samples.

As illustrated in Table 4, the inventive methodology produced extremely reliable results, compared to standard/conventional culture methods. Moreover, as illustrated by the samples that include the *** indication, the claimed methodology was also able to reveal the presence of an AR marker, which was not detected using the traditional culture methodology. Moreover, as illustrated in Table 5, by detecting organisms that were not previously detected using traditional culture-based methods, the method further shows increased sensitivity compared to the culture-dependent methodology.

As illustrated in Tables 6, 7, and 8, the inventive methodology was used to identify microorganisms from different sample types. For example, in Table 6, the inventive methodology was used to identify the listed species and the listed antibiotic resistances in 27 respiratory specimen samples from subjects with cystic fibrosis. Similarly, in Table 7, the inventive methodology was used to identify the listed species and the listed antibiotic resistances in 24 respiratory specimen samples from subjects with chronic rhinosinusitis. Finally, in Table 8, the inventive methodology was used to identify the listed species and the listed antibiotic resistances in 38 respiratory specimen samples from subjects with various respiratory diseases.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

TABLE 1

Oligonucleotides/Primers for Use in Identifying Bacterial Species

| Target purpose | Target ID | Assay | Sequence | SEQ ID NO: |
|---|---|---|---|---|
| Species ID | Klebsiella pneumoniae | Kp_M1_UT1v (Cluster 1245) | CGTTTCACAACTGCGGATG | 1 |
| | | | TGGCGGTCATGTTCTTACTC | 2 |
| | | Kp_M1_UT2v (Cluster 1245) | TTCACACCGCCATCGTC | 3 |
| | | | CAGCATCTCCACCGACAG | 4 |
| | | Kp_M1_UT1nv (Cluster 4240) | CGTTCCTCACCGTAGTGG | 5 |
| | | | TCCAGCGTGACATAATCGG | 6 |
| | | Kp_M1_UT2nv (Cluster 4240) | TTTCCACCTACGCCGATAAAG | 7 |
| | | | CCAGCGGAATAACCAGGAC | 8 |
| | | Kp_M2_UT1v (Cluster 1825) | GGCGGCGATGAGTTTGT | 9 |
| | | | ATGTTGCGGATAGCCTGATAG | 10 |
| | | Kp_M2_UT2v (Cluster 1825) | CGCTCCACTATCAGGCTATC | 11 |
| | | | TTCGGCGATGGGAATAAACA | 12 |
| | | Kp_M2_UT1nv (Cluster 2858) | TGCCTATCGCCACTTTATTGA | 13 |
| | | | CGGTCGTTAATCGCCTTCT | 14 |
| | | Kp_M2_UT2nv (Cluster 2858) | CCTCAGGTACGCTCATTCG | 15 |
| | | | TCGTCACATCCCTCCTCTT | 16 |
| | Species IDSerratia marcescens | Smar_UT1 | GATCAGCAGCAAACGGTGAC | 17 |
| | | | GGCGATGTAATCCTGCGAGA | 18 |
| | Species IDProteus mirabilis | Pmbs_UT1 | GGGATATCCGTGGAATGCGT | 19 |
| | | | TAATGTGATCACCGCTCCCG | 20 |
| | Species IDProvidencia alcalifaciens | Pal_UT1 | ACGAGCCAGCCTGATGAAAA | 21 |
| | | | CATCGCAACTGCTGCATCTC | 22 |
| | Species IDProvidencia stuartii | Pst_UT1 | GCCTTGCGCCTTAGTTTGTT | 23 |
| | | | GGCTATCCATTTTCCAGCCG | 24 |
| | Species IDEnterococcus faecalis | Efs_UT1 | TTCTTTTCCAGGAGCAACGC | 25 |
| | | | AGCAAGACAGAAATAAGTAAAAAGA | 26 |
| | | Efs_UT2 | TCTTCGTCATGGTGSGTTTC | 27 |
| | | | AACGGAACATGGTGAGCAAC | 28 |
| | Species IDEnterococcus faecium | Efm_UT1 | GKTTTGATGGCTGGGTCAGT | 29 |
| | | | TGTTTGGCTTTTTGCAGTTG | 30 |
| | | | TACTTRGCTTTTTGCAGTTG | 31 |
| | | Efm_UT2 | TCAGTGAAAACRACCCACGA | 32 |
| | | | ATYGCTGCTGTCCGAGTTCT | 33 |
| | Species IDKlebsiella oxytoca | Koxy_UT2 | CCGTCGCCGTATTACTGAT | 34 |
| | | | TCTCTACAACACGCTACCCTA | 35 |
| | Species IDKlebsiella oxytoca | Koxy_UT3 | GGTGAGAACGATGTGATTGTG | 36 |
| | | | TGACCCAAAGGCGATTCG | 37 |
| | Species IDPseudomonas aeruginosa | PSAR_28621 | GAAGCGGTTGAGGAACAG | 38 |
| | | | ACCCACGACATGATGTAC | 39 |
| | | PSAR_27569 | GGACGATCCATTCCATACCG | 40 |
| | | | GACGAAGCGGTGATCCAC | 41 |
| | Species IDStaphylococcus aureus | Sa_M1_UT1 | ATAGGTGTGGCTTTTGTAGGG | 42 |
| | | | CTGCTGCTAATAACGCTTGC | 43 |
| | | Sa_M2_UT1 | ATGGTTATGAAATTGTTGGTGATGAA | 44 |
| | | | CCGTTGCTTGATATTCTTTCGTAT | 45 |
| | | Sa_M4_UT1 | TACGAAATCAGAAGTGGCTCAA | 46 |
| | | | ACGTTAAATCCTGCATTTTCCAA | 47 |
| | | Sa_M4_UT2 | TAGCGTTGGTATTAAGTGGTTGT | 48 |
| | | | GTCATAGCATAGTTCGGGTCA | 49 |

TABLE 1 -continued

Oligonucleotides/Primers for Use in Identifying Bacterial Species

| Target purpose | Target ID | Assay | Sequence | SEQ ID NO: |
|---|---|---|---|---|
| Genus and species ID | Staphylococcus | tuf_UT1 | ACWGGCCGTGTTGAACGTG | 50 |
| | | | CACCAGCTTCAGCGTAGTCTAAT | 51 |
| | | tuf_UT2 | CTCAACWGGCATCATGAATGGTTT | 52 |
| | | | AGGTGACGATGTRCCTGTAATC | 53 |
| Species ID | Escherichia coli | Ec_M1_UT | CGTTGTTTGCGACCYGTATA | 54 |
| | | | AATGTAAATTCGCTGRGATCGT | 55 |
| | | Ec_M2_UT | CGCCTGGCTCTGTTTCA | 56 |
| | | | AGCAAGTGCATTACGAGTCT | 57 |
| Species ID | Acinetobacter baumannii | AB_marker1 | GTCTGTTGAATGATGATGTATGTCG | 58 |
| | | | ATCCCATTTTACAAATGGCAAAACA | 59 |
| | | | TGCAGAACTAGCCCATTTTACA | 60 |
| | | | TGCWGAACTAKCCCATTTTACA | 61 |
| Species ID | Acinetobacter baumannii | Ab_M2_UT1 | TTTAGCGRACAGATTTGGTTTACA | 62 |
| | | | CGGTTGCCTTGCTGAGTT | 63 |
| | | Ab_M2_UT2 | TCCGYAAACCTCAACTCATTT | 64 |
| | | | GCCAGTGAACCATCTAATACAGT | 65 |
| | | Ab_M3_UT1 | TAGAGCAGCAACAAATCAACAAGA | 66 |
| | | | TTATTATGAGTCGCCTTGGCAATT | 67 |
| | | Ab_M3_UT2 | TAGAGCAGCAACAAATCAACAAGA | 68 |
| | | | TCGCATGGCTTCTGACTCA | 69 |
| | Acinetobacter calcoaceticus-baumannii complex | Acb_M2_UT1 | AAATTGCYAAAGCACAAGGTTT | 70 |
| | | | CGGGAATTGCYTCATGGTAAG | 71 |
| | | Acb_M3_UT1 | GATAGCGATTACTCGGTTCCATC | 72 |
| | | | CCTGTGCCTAAAACCAGTGAAA | 73 |
| Species ID | Streptococcus pneumoniae | Sp_M1_UT2 | TCCTGATATAATCGGTGTCACAAG | 74 |
| | | | AGAACAAGAGGTATGCATCTAACTT | 75 |
| | | Sp_M2_UT1 | CTGATGGATATGGAGACATTAAGGAT | 76 |
| | | | GTCCAATTATATGCGGATCTATACCT | 77 |
| | | Sp_M2_UT2 | CTGATGGATATGGAGACATTAAGGAT | 78 |
| | | | AATTAGTTGAGTAGCCATGACAGT | 79 |
| | | Sp_M3_UT1 | TACGGTGTAAGTGCTGATAAAGG | 80 |
| | | | GCTTCAAAGTTAAGTCCATCCAAAT | 81 |
| Species ID | Streptococcus agalactiae | GBS_UT1 | GCCAACCGTGGTATGTCA | 82 |
| | | | TTCTGCCGGGTTTCTTTG | 83 |
| | | GBS_UT2 | CTCGTGCTGCTACTTCTC | 84 |
| | | | CGTGGATGTGCTYGTTAACAAC | 85 |
| Species ID | Enterobacter cloacae group | Encl_M1_UT | AACTTRTCCTTGTGCTTGC | 86 |
| | | | ACATAGTCGTTGGCATACAGA | 87 |
| | | | ATTGTTGATGACTGTTCCTCTTC | 88 |
| | | | CGACGAYGATGACGAATG | 89 |
| | | | CGCAATTAAGTCGGTCCTG | 90 |
| Species ID | Enterobacter cloacae group | Encl_M2_UT | CCTTCAACGTGRATGTTCAG | 91 |
| | | | AATWCCYACTTCGCCTTCA | 92 |
| | | | TGGCGTTCTGGAYGTCAA | 93 |
| | | | AGTTGTTTATACCGCCAAAGC | 94 |
| | | | AGTTGTCTACACTGCCAAAGC | 95 |
| Species ID | Enterobacter aerogenes | Eaer_M1_UT | ACCCAAAAGTATTCTGATTGTTGAG | 96 |
| | | | ATGAGGTCTTATTATCGGTCAACTG | 97 |
| Species ID | Enterobacter aerogenes | Eaer_M2_UT | AATCGGCAATACCAGCAGTT | 98 |
| | | | CCTTCACGGAATAACATATCCAGAT | 99 |
| Species ID | Streptococcus pyogenes | Spyo_UT1 | GCTTATTGCTAATGACTGTGCTTAT | 100 |
| | | | TGCCGACATTGACAACCATA | 101 |
| Species ID | Streptococcus dysgalactiae | Sdys_UT1 | CATCTGCTTGACCTTTATGAAAC | 102 |
| | | | GTGAGGCTAACACATCAAACTAG | 103 |
| Species ID | Streptococcus dysgalactiae | Sdys_UT2 | ATGCGGGAGGTCTGTTTCTAC | 104 |
| | | | CCAGCCGGTAAAGAAACTC | 105 |
| Species ID | Streptococcus equi | Sequi_UT1 | GTCAAGCACCTTAYCACCATCTAG | 106 |
| | | | GGCATGCTTGTGAACAACA | 107 |

TABLE 1 -continued

Oligonucleotides/Primers for Use in Identifying Bacterial Species

| Target purpose | Target ID | Assay | Sequence | SEQ ID NO: |
|---|---|---|---|---|
| Species ID | Streptococcus equi | Sequi_UT2 | GTGCCRATTGAGGATCTGGTTTC | 108 |
| | | | CYGTTGGACCACTTCCTGTCAT | 109 |

TABLE 2

Oligonucleotides/Primers for Use in Identifying Antibiotic Resistance in Bacteria

| Target purpose | Target ID | Assay | Sequence | SEQ ID NO: |
|---|---|---|---|---|
| B-lactam resistance | blaKPC | KPC_UT1 | CGTCTAGTTCTGCTGTCTTGT | 110 |
| | | | ACCGTCATGCCTGTTGTC | 111 |
| | | KPC_UT2 | TTGTTGATTGGCTAAAGGGAAAC | 112 |
| | | | CAGACGACGGCATAGTCATT | 113 |
| B-lactam resistance | blaNDM | NDM_UT1 | GGACAAGATGGGCGGTATG | 114 |
| | | | CGGCGTAGTGCTCAGTG | 115 |
| | | NDM_UT2 | CAACTGGATCAAGCAGGAGAT | 116 |
| | | | CGACAACGCATTGGCATAAG | 117 |
| Aminoglycoside resistance | rmtA | rmtA_UT1 | GAATTGGACTGCCTCTACGATT | 118 |
| | | | GCACGCCCATACAGATGT | 119 |
| Aminoglycoside resistance | rmtB | rmtB_UT1 | AAGGCATGGAGGCGAAC | 120 |
| | | | AAGTATATAAGTTCTGTTCCGATGGT | 121 |
| Aminoglycoside resistance | rmtC | rmtC_UT1 | AATACTCCACACTTTATCCACCAA | 122 |
| | | | TTCTTGCGAACCTCCTTCTC | 123 |
| Aminoglycoside resistance | rmtD1 and rmtD2 | rmtD1_&_D2 | AACGATGCGACGATCCATT | 124 |
| | | | GCGATTTGCTGTGCGAAA | 125 |
| Aminoglycoside resistance | npmA | npmA | CCGCTTGCTGGTACATATCTA | 126 |
| | | | CCTATCTCGTCCGCTATCTG | 127 |
| Aminoglycoside resistance | armA | armA | ACTATTCTGCCTATCCTAATTGGG | 128 |
| | | | TCATTTAATGTTGCGACTCTTTCA | 129 |
| fluoroquinolone resistance | gyrA | gyrA_ACBA_UT1 | ATGACTATAACAAAGCYTACAAGAAATC | 130 |
| | | | ACAATGGTTTCATAAACAGCTAAGTC | 131 |
| | | gyrA_PSAR_UT1 | AACAAGCCCTACAAGAAATCC | 132 |
| | | | CGCACTTCGGTGTATCG | 133 |
| | | gyrA_PSAR_UT2 | AACAAGCCCTACAAGAAATCC | 134 |
| | | | CTCGGTGCCATCGTAGT | 135 |
| | | gyrA_staph_UT1 | CATTGCCAGATGTTCGTGAC | 136 |
| | | | GCCATCAACAAGCGGATAAC | 137 |
| | | gyrA_Ecoli_UT1 | AAATCTGCCCGTGTCGTT | 138 |
| | | | ACCATCCACCAGCATGTAAC | 139 |
| | | gyrA_Ecoli_UT2 | CTCCTATCTGGATTATGCGATGT | 140 |
| | | | CGTCAATAGAACCGAAGTTACC | 141 |
| | | gyrA_Kleb_UT1 | CAATGACTGGAACAAAGCCT | 142 |
| | | | CGATGGAACCAAAGTTACCC | 143 |
| fluoroquinolone resistance | parC | parC_PSAR_UT1 | TTGTAGTGTTCCAGGTCGTC | 144 |
| | | | CCGTCTGCTATTGTTCAAGG | 145 |
| | | parC_Kleb_UT1 | GAAATTCAAAAAGTCCGCCC | 146 |
| | | | GGATAGCGGTAAGAGAACGG | 147 |
| | | parC_Kleb_UT2 | CAGCGCGAAATTCAAAAAGT | 148 |
| | | | GCGAAAGATTTGGGATCGTC | 149 |
| | | parC_Ecoli_UT1 | GTTCTCTTACCGTTATCCGC | 150 |
| | | | TATTTCGACAACCGGGATTC | 151 |
| | | parC_Ecoli_UT2 | TGTGTATGCGATGTCTGAAC | 152 |
| | | | ATATTTCGACAACCGGGATTC | 153 |
| | | parC_ACBA_UT1 | GAGCGAGCTAGGCTTAAAAA | 154 |
| | | | TCCCCTGACCTTCGATTAAA | 155 |
| | | parC_ACBA_UT2 | GTACGTCATTATGGACCGTG | 156 |
| | | | CTATAAGCCGAGAGTTTGGC | 157 |
| | | parC_staph_UT1 | TCCGTAAAAGTGCGAAAACA | 158 |
| | | | AGCTTCAGTGTAACGCATTG | 159 |
| | | parC_staph_UT2 | CCAGATGTTCGTGATGGTTT | 160 |
| | | | CTTAGCTTCAGTGTAACGCA | 161 |

TABLE 2 -continued

Oligonucleotides/Primers for Use in Identifying Antibiotic Resistance in Bacteria

| Target purpose | Target ID | Assay | Sequence | SEQ ID NO: |
|---|---|---|---|---|
| Fluoroquinolone resistance | QnrA | qnrA_UT1 | TAGAGTTCAGGGAGTGCGAT | 162 |
| | | | CCGAGCAGAAGTACATCTTATGG | 163 |
| | | qnrA_UT2 | GATTTGAGYGACAGCCGTTT | 164 |
| | | | GCAGAAGTACATCTTATGGCTGA | 165 |
| Fluoroquinolone resistance | QnrC | qnrC_UT1 | GCTAATTTCTCACAGGCAAACTTT | 166 |
| | | | ACAACCCGTAATGTAAGCAGAG | 167 |
| | QnrD | qnrD_UT1 | GTTTGATTGGTCTTTGGCTGATT | 168 |
| | | | CCATCCAACTTCACTCCATCT | 169 |
| | | qnrD_UT2 | CGACAGGAATAGCTTGGAAGG | 170 |
| | | | CCAGTTATCACAGTGCCATTC | 171 |
| | QnrS | qnrS_UT1 | CAATTTATGCCACGCCGAAC | 172 |
| | | | TAATTTATGTCACGCCGAAC | 173 |
| | | | GATAAACAACAATACCCAGTGCTT | 174 |
| | | qnrS_UT2 | GTGCTAACTTGCGTGATACGA | 175 |
| | | | TCCATATTGGCATAGGAAAGATTACA | 176 |
| | | | TCCATATTGGCATAAGACAGGTTACA | 177 |
| | QnrB | qnrB-C1_UT1 | GACGTTCAGTGGTTCRGATCT | 178 |
| | | | KGCTCGCCAGTCGAAAGT | 179 |
| | | qnrB-C1_UT2 | CGACGTTCAGTGGTTCRGATCT | 180 |
| | | | GCKGCTCGCCAGTCGAAA | 181 |
| | | qnrB-02_UT1 | ACCAATCTAAGCTACGCCAACTT | 182 |
| | | | CCTGAGTTCCCATCCAGCG | 183 |
| | | qnrB-03_UT1 | TACGCACTGTGATTTGACCAAT | 184 |
| | | | GGAKCAACGATGCCTGGTAG | 185 |
| | | qnrB-03_UT2 | CGCATATATCACCAATACCAACTT | 186 |
| | | | GTTCCAGGAKCAACGATGCC | 187 |
| B-lactamase production | blaCTX-M genes | CTX-M-G1_64_UT1 | CCGTCACGCTGTTGTTAGG | 188 |
| | | | CGCTCATCAGCACGATAAAGT | 189 |
| | | CTX-M-G1_64_UT2 | CGCTGATTCTGGTCATTTACTTC | 190 |
| | | | ACGGCTTTCTGCCTTAGGT | 191 |
| | | CTX-M-G1_UT1 | CGATGTGCAGCACCAGTAA | 192 |
| | | | TCGGTTCGCTTTCACTTTTCT | 193 |
| | | CTX-M-G1_UT2 | GACGATGTCACTGGCTGAG | 194 |
| | | | CCACAACCCAGGAAGCAG | 195 |
| | | CTX-M-G2_74-75_UT1 | TGGCGCAGACCCTGAAAA | 196 |
| | | | ATATCGTTGGTGGTGCCATAA | 197 |
| | | CTX-M-G2_74-75_UT2 | ATGGCGCAGACCCTGAAA | 198 |
| | | | CCGCTGCCGGTTTTATCG | 199 |
| | | CTX-M-G8_G25_UT1 | GAGCCGACGCTCAACACC | 200 |
| | | | CCCGACAACCCACGATGT | 201 |
| | | CTX-M-G8_G25_UT2 | GCTCAACACCGCGATCCC | 202 |
| | | | CCCGACAACCCACGATGT | 203 |
| | | CTX-M-G9_UT1 | TTCGTCTGGATCGCACTGA | 204 |
| | | | GATGATTCTCGCCGCTGAAG | 205 |
| | | CTX-M-G9_UT2 | CGCTGGTTCTGGTGACCTA | 206 |
| | | | GATGATTCTCGCCGCTGAAG | 207 |
| Dihydrofolate reductase production (DNA synthesis) uninhibited by trim ethoprim | dfrA genes | dfrA1_UT1 | AATGGCTGTTGGTTGGACG | 208 |
| | | | CATACTTTCGGTTGGGTAATGCT | 209 |
| | | dfrA15_UT1 | AATATGCCGTTGTAACTCGTTCA | 210 |
| | | | ACACAATCACATGATCCGTTATCG | 211 |
| | | dfrA16_UT1 | AGTATGCAGTTGTAACTCGCTCTA | 212 |
| | | | CACCACCACCAGAAACGATAAC | 213 |
| | | dfrA14-30_UT2 | GTGATTGGTTGCGGTCCA | 214 |
| | | | CCCGCCACCAGACACTAT | 215 |
| | | dfrA6-31_UT1 | YGAGAATGGAGTAATTGGCTCT | 216 |
| | | | WATTTCACCACCACCAGAAACAAA | 217 |
| | | dfrA26-13_UT1 | GGGWGCCAATCGGGTTAT | 218 |
| | | | CTCAGTGAGTCTGCGAAA | 219 |
| | | | CTCGGTGAGCCTGCGAAA | 220 |
| | | dfrA8_UT1 | AAAGACTACGAGCAGAATGGC | 221 |
| | | | ACGGTAAGTGAAGTAAGTGTGAAG | 222 |
| | | dfrA3b_UT1 | AACGCTGCCATTGTTACCA | 223 |
| | | | AAGCCTTGAAGTGTTCTGGAG | 224 |
| | | dfrA9_UT1 | AAGACAGGAGGTATCGGATTTGA | 225 |
| | | | CGTAGGCAGCTAAGTTCTCGTA | 226 |
| | | dfrA24_UT1 | AAGACCGCATCAATATCGTCATC | 227 |
| | | | CATAGCAAGCCGTCCAAGAA | 228 |
| | | dfrA27-28_UT1 | AAGACTCTTACGAACCATGTTGTT | 229 |
| | | | CCTCTGGCTCGGAATCTATTG | 230 |
| | | dfrA25_UT1 | AAGCACTGACCTATAACCAATGG | 231 |
| | | | CCCAGGAATGTTCGGAAAGAAA | 232 |

TABLE 2 -continued

Oligonucleotides/Primers for Use in Identifying Antibiotic Resistance in Bacteria

| Target purpose | Target ID | Assay | Sequence | SEQ ID NO: |
|---|---|---|---|---|
| | | dfrA10_UT1 | AAGCATTCAGAGACACAACCAA | 233 |
| | | | AACCAACACCACCAATGACAT | 234 |
| | | dfrA32_UT1 | AAGGTGAGCAGCTAATCTTTAAGG | 235 |
| | | | TGACCCTGAAATTCCATTCTTTGA | 236 |
| | | dfrA20_UT1 | AAGTCGCACAACATCTTGAAGG | 237 |
| | | | AGATTTGAGCACCACCAATAATGA | 238 |
| | | dfrA23_UT1 | AATCAATATCACGACAGCGATCAA | 239 |
| | | | CTTCACGGGATGGGTCTCA | 240 |
| | | dfrA7_UT1 | AATCAGTGGCTCCTTGTTGG | 241 |
| | | | GGAAGAACACCCATAGAGTCAAAT | 242 |
| | | dfrA29_UT1 | AATCAGTGGCTTCTTGTCGG | 243 |
| | | | GTGGATGATAGATAAGTGGATGGT | 244 |
| | | dfrA17_UT1 | AATGGCGTAATCGGTAGTGG | 245 |
| | | | GCTTGAAATTCCGTTCTTTGACA | 246 |
| | | dfrA18_UT1 | ACGCATTGCTGTCATTGGT | 247 |
| | | | CTCGCTGGCACTGGAATC | 248 |
| | | dfrA3_UT1 | ACTCTATGCCGAGGCTCTG | 249 |
| | | | CGCTGACGACTCAAGGTAAC | 250 |
| Dihydrofolate reductase production (DNA synthesis) uninhibited by trimethoprim | dfrB genes | dfrB1-8_UT1 | WATGGAGATCGCGTGCG | 251 |
| | | | GCWGTACCACCCGACAATCT | 252 |
| | | dfrB2-7_UT1 | GCAGGGTCAAGTYGTCGG | 253 |
| | | | TCGGACTCGACSGCATAG | 254 |
| | | dfrB3_1_UT1 | ACCCGACAACTTGACCCT | 255 |
| | | | ACCAACACAACAATGGAGTCA | 256 |
| | | dfrB4_UT1 | AATCTCACCCAGGCTCAGT | 257 |
| | | | CCGTTCAAGCGCAGTCAT | 258 |
| dihydropteroate synthase (DNA synthesis) uninhibited by sulfonamides | sul genes | sul1_UT1 | GCTGGTGGTTATGCACTCAG | 259 |
| | | | CGCCCAAGAAGGATTTCCG | 260 |
| | | sul1_UT2 | CGTGCTGTCGAACCTTCAA | 261 |
| | | | GCTGGACCCAGATCCTTTACA | 262 |
| | | sul2_UT1 | CATCATTTTCGGCATCGTCAAC | 263 |
| | | | GCGACAAGGCATAGGCTT | 264 |
| | | sul2_UT2 | GTCAACATAACCTCGGACAGTT | 265 |
| | | | CTCGGCCATCAGCTTACG | 266 |
| | | sul3_UT1 | AAAGCCTTAATGACAGGTTTGAGT | 267 |
| | | | GAAGATGGAGCAGATGTGATTGAT | 268 |
| | | sul3_UT2 | GGCAAAGTCAGATTGCAAACTTG | 269 |
| | | | CCTCTTCCGGATTCGTTTCAAC | 270 |
| Vancomycin-intermediate S. aureus (VISA) | Staphylococcus rpoB (VISA) | VISA_rpoB-481_UT1 | CCAGGTCCTAATGCTGATAGACG | 271 |
| | | | ACCGTCGTTTACGTTCTGTAGGTG | 272 |
| | | VISA_rpoB-481_UT2 | CCAGGTCCTAATGCTGATAGACG | 273 |
| | | | GGACCAAGCAAAYCCATTAGCT | 274 |
| Staphylococcus antibiotic resistance | linA | linA_UT1 | GTGAAGGCATCCAATSAACTT | 275 |
| | | | AAACMACAAAGAGAACACAGAGAT | 276 |
| | mecA | mecA_UT1 | GGAACGATGCCTATCTCATATGCT | 277 |
| | | | ATAGCGTCATTATTCCAGGAATGCA | 278 |
| | vanA | vanA_UT1 | CGGCTCGACTTCCTGATGA | 279 |
| | | | TGTGCGGTATTGGGAAACAG | 280 |
| | aacA | aacA_UT1 | GCCACACTATCATAACCACTACCGA | 281 |
| | | | TCCAAGAGCAATAAGGGCATACCAA | 282 |
| | blaZ | blaZ_UT1 | ACACTCTTGGCGGTTTCACT | 283 |
| | | | CCTAAGGGCCAATCTGAACCTATT | 284 |
| | ermA | ermA_UT1 | CAACCATTGATTTCAAAGAAGGACTAC | 285 |
| | | | TCAAAGCCTGTCGGAATTGGT | 286 |
| | ermC | ermC_UT1 | ATTTAATCGTGGAATACGAGTTTGCTAA | 287 |
| | | | CGTCAATTCCTGCATGTTTTAAGG | 288 |
| | tetK | tetK_UT1 | AGTTTGAGCTGTCTTGGTTCATTG | 289 |
| | | | TGCAGCAGATCCTACTCCTTGTAC | 290 |
| | tetM | tetM_UT1 | CTTTCTGGGCTTCCATTGGTTTATC | 291 |
| | | | CGAGCTCTCATACTGCATTCCA | 292 |
| | msrA | msrA_UT1 | CTTCTTCCAAATGTTCCATTCTTTTT | 293 |
| | | | ACCAGATCGTTTAAGTGCATCAAA | 294 |
| | cfr | cfr_UT1 | AACGAAGGGCAGGTAGAAGC | 295 |
| | | | TGACCACAAGCAGCGTCAAT | 296 |
| | | cfr_UT2 | GTGAGGAACGCAGCAAATTGA | 297 |
| | | | GCTTCTACCTGCCCTTCGTT | 298 |

TABLE 3

Oligonucleotides/Primers for Use in Genetic Characterization of Bacteria

| Target purpose | Target ID | Assay | Sequence | SEQ ID NO: |
|---|---|---|---|---|
| MRSA ID-orfX junction | MRSA-orfX | MRSA-orfX_UT1 | GGATCAAACGGCCTGCACA | 299 |
| MRSE ID-orfX junction | MRSE-orfX | MRSE-orfX_UT1 | TGGCTCCAATGGTYTACACCAA | 301 |
| | | | GTCAAAAATCATGAACCTCATTACTTATG | 302 |
| | | | ATTTCATATATGTAATTCCTCCACATCTC | 303 |
| | | | CAAATATTATCTCGTAATTTACCTTGTTC | 304 |
| | | | CTCTGCTTTATATTATAAAATTACGGCTG | 305 |
| | | | CACTTTTTATTCTTCAAAGATTTGAGC | |
| SCCmec typing | S. aureus ccrB2 | SCCmec_ccrB2_UT | CTCATGTTACARATACTTGCG | 306 |
| | | | CCTTGATAATAGCCTTCTTGG | 307 |
| | S. aureus mecl | SCCmec_mecl_UT | CGTTATAAGTGTACGAATGGTTTTTG | 308 |
| | | | TCATCTGCAGAATGGGAAGTT | 309 |
| | S. aureus IS1272J | SCCmec_IS1272J_UT | GAAGCTTTGGGCGATAAAGA | 310 |
| | | | GCACTGTCTCGTTTAGACCAATC | 311 |
| | S. aureus ccrC | SCCmec_ccrC_UT | TCCAGTCTATAAAGGSTATGTCAG | 312 |
| | | | ACTTATAATGGCTTCATGCTTACC | 313 |
| | S. aureus ccrB1 | SCCmec_ccrB1_UT | ACCACAAACACACTTAAAGATG | 314 |
| | | | CAATTTCAAGTATTTGGTCCATAAC | 315 |
| | S. aureus ccrB3 | SCCmec_ccrB3_UT | AACACAACGAACACATTGAAAG | 316 |
| | | | CGTATTTCTCAATCACATCAGC | 317 |
| | S. aureus ccrB4 | SCCmec_ccrB4_UT | CGAAGTATAGACACTGGAGCGATA | 318 |
| | | | GCGACTCTCTTGGCGTTTA | 319 |
| | S. aureus mecC2 | SCCmec_mecC2_UT | TCAGTTCATTGCTCACGATATG | 320 |
| | | | GCCAACGGCTACAGTGATAA | 321 |
| | SCCmeclVa-J1 | SCCmeclVa-J1_UT | CAGGATATTTTTCAAACTCCTTCA | 322 |
| | | | TGGAGGACCAAGGATATTCG | 323 |
| | SCCmeclVa | SCCmeclVa_UT | CCTTTGAATGCCCTCCATGAATAAAAT | 324 |
| | | | GCATATAGAAAAGATAGAAGTTCGAAAGA | 325 |
| S. aureus virulence | MRSA sea | sea_UT | TATGGCTAGACGGTAAACAAAATACAG | 326 |
| | | | CTCTGAACCTTCCCATCAAAAACATC | 327 |
| | MRSA seb | seb_UT | TTACTGTTMGGGTATTTGAAGATGG | 328 |
| | | | CCGTTTCATAAGGYGAGTTGT | 329 |
| E. coli virulence | Shiga toxin genes | stx1_UT | ATGTCAGAGGGATAGATCCA | 330 |
| | | | TATAGCTACTGTCACCAGACAAT | 331 |
| | | stx2_UT | AGTTCTGCGTTTTGTCACTGTC | 332 |
| | | | CGGAAGCACATTGCTGATT | 333 |
| | E. coli aggR | EAEC_aggR_UT | GATACATTAAGACGCCTAAAGGATGC | 334 |
| | | | CCTTTTGACCAATTCGGACAACT | 335 |
| | T3SS in E. coli | escV_UT | TGGAATAATCATCATCATTACAGCCA | 336 |
| | | | GAGTCATATCACGATCTTATTCTGGC | 337 |
| | E. coli virulence | bfpA_UT | TACCAGTCTGCGTCTGATTCC | 338 |
| | | | ACGTTGCGCTCATTACTTCTG | 339 |
| | E. coli (and Shigella) invasion antigen | EIEC_lpaH3_UT | TGAGTTACCTGAATCACTGGAAG | 340 |
| | | | TCGAGGATGATAGTGCAGGTC | 341 |
| | E. coli enterotoxins | ETEC_eltA_UT | CTGCGTTAGGTGGAATACCAT | 342 |
| | | | CTGGGTCTCCTCATTACAAGTATC | 343 |
| | | ETEC_estA_UT | GTTCCAGCCTGCCATCTG | 344 |
| | | | TCGCCAGCAACACTTCAG | 345 |
| | E. coli UPEC | UPEC_fyuA_UT | AAGCACGCTGGTGGTTAC | 346 |
| | | | CTGGATGGTGTTGGTGGAA | 347 |
| Klebsiella capsule type | wzi gene of cps locus | wzi_UT | CGCGAGYGCTTTCTATCTTG | 348 |
| | | | GAGASCCACTGGTTCCAGAA | 349 |
| CONTROL PCR | IPSC | PSC_UT1 | ACCCAACTGAATGGAGCGGGCGGA CGAAAACCCTTGAGCACAG | 350 |
| | | | ACGCACTTGACTTGTCTTCGCCGGG ATGCCTTACCTAGACGCAATGA | 351 |
| | | | ACCCAACTGAATGGAGCGCGGCAGC CGTTGAGGCAAAAGTGATAC | 352 |
| | | PSC_UT2 | ACGCACTTGACTTGTCTTCCGAGTTC CGTCCGGTTAAGCGTGACAGTC | 353 |

TABLE 4

Organisms Detected Correctly Compared to Culture Methods

Organisms Detected Correctly Compared to Culture Methods/Total Tested

| Specimen Type | K. pneumoniae | S. aureus | S. pneumoniae | P. aeruginosa | E. coli | A. baumannii | None** |
|---|---|---|---|---|---|---|---|
| Respiratory | 4/4\* | 4/4 | 2/2 | 4/4 | 2/2 | 1/1** | 4/10 |
| Urine | 9/9\*** | | | | 1/1 | | 0/1 |
| Wound | 1/1 | 3/3 | | | | | 2/2 |
| Nasal Swab | | 5/5 | 3/3 | 1/1 | | | 2/4 |

\**None, Negative culture results or culture detected other organisms
Bold-face type indicates antibiotic resistance genes detected by amplicon sequencing
\***In one sample, the inventors found a fluoroquinolone-conferring mutation in the gyrA gene.

TABLE 5

False Positives

False Positives*

| Specimen Type | K. pneumoniae | S. aureus | S. pneumoniae | P. aeruginosa | E. coli | A. baumannii |
|---|---|---|---|---|---|---|
| Respiratory | 1 | 3 | 0 | 0 | 1 | 1 |
| Urine | | | | | 1 | |
| Wound | | | | | | |
| Nasal Swab | | 2 | 0 | 0 | | |

*Detected by methodology when culture was negative or detected other organisms.

TABLE 6

Identification of Bacterial Species and Antibiotic Resistances in 27 Respiratory Specimen Samples from Subjects with Cystic Fibrosis Bacterial Species Identified in Respiratory Specimen Samples

| Bacteria Identified | Number of Identifications |
|---|---|
| P aeruginosa | 22 |
| E. coli | 2 (UPEC) |
| MRSA | 15 (9 CC5, SCCmecII) |
| MRSE | 11 |
| MSSA | 1 |
| S. pneumoniae | 2 |
| A. baumannii | 2 |
| GBS | 5 |
| E. faecalis | 2 |
| Other Staphylococcus species | 3 |
| P. mirabilis | 2 |
| Negative | 2 |

Antibiotic Resistance

| Antibiotic Resistance | Number of Identifications |
|---|---|
| Macrolides | 10 |
| Fluoroquinolones | 3 |
| Trimethroprim-sulfamethoxazole | 5 |
| Clindamycin | 1 |

TABLE 7

Identification of Bacterial Species and Antibiotic Resistances in 24 Respiratory Specimen Samples from Subjects with Chronic Rhinosinusitis Bacterial Species Identified in Respiratory Specimen Samples

| Bacteria Identified | Number of Identifications |
|---|---|
| P aeruginosa | 9 |
| MRSA | 7 (1 CC5/SCCmecII, several SCCMecIVa, 1 USA300, 5 SCCmecV) |
| MRSE | 19 (several SCCmecIVa) |
| MSSA | 5 (3 CC8) |
| E. faecalis | 1 |
| E. faecium | 1 |
| Other Staphylococcus species | 2 |
| P. mirabilis | 6 |
| E. aerogenes | 2 |
| K. pneumoniae | 1 (CG258) |

Antibiotic Resistance Found

| Antibiotic Resistance | Number of Identifications |
|---|---|
| Aminoglycosides | 11 |
| ESBL | 9 |
| Macrolides | 31 |
| Fluoroquinolones | 15 |
| Trimethroprim-sulfamethoxazole | 12 |
| Clindamycin | 4 |
| Tetracycline | 8 |
| Vancomycin | 2 |

TABLE 8

Identification of Bacterial Species and Antibiotic Resistances in 38 Respiratory Specimen Samples from Subjects with Various Respiratory Diseases Bacterial Species Identified in Respiratory Specimen Samples

| Bacteria Identified | Number of Identifications |
|---|---|
| P aeruginosa | 8 |
| MRSA | 6 (4 SCCMecIVa, 3 USA300) |
| MRSE | 4 (1 SCCmecIVa) |
| MSSA | 6 (1 005) |
| E. faecalis | 8 |
| E. faecium | 1 |
| Other Staphylococcus species | 8 (2 SCCmecIVa) |
| S. pneumoniae | 4 |
| A. baumannii | 3 |

TABLE 8-continued

Identification of Bacterial Species and Antibiotic Resistances in 38 Respiratory Specimen Samples from Subjects with Various Respiratory Diseases

| | |
|---|---|
| P. mirabilis | 1 |
| E. aerogenes | 1 |
| E. cloacae | 3 |
| K. pneumoniae | 4 |
| E. coli | 4 |
| K. oxytoca | 2 |
| GBS | 1 |
| Negative | 2 |

TABLE 8-continued

Identification of Bacterial Species and Antibiotic Resistances in 38 Respiratory Specimen Samples from Subjects with Various Respiratory Diseases Antibiotic Resistance Found

| Antibiotic Resistance | Number of Identifications |
|---|---|
| Aminoglycosides | 1 |
| Macrolides | 11 |
| Fluoroquinolones | 7 |
| Trimethroprim-sulfamethoxazole | 4 |
| Clindamycin | 1 |
| Tetracycline | 3 |

TABLE 9

Oligonucleotides of Lineage Identification Assays

| Target purpose | Target ID | Assay | Sequence | SEQ ID NO: |
|---|---|---|---|---|
| Streptococcus pyogenes M59 | M59 | M59_UT1 | AGAGGAGGAGATAGAGTAGGAGAT | 354 |
| | | | TACCAGCCAGTATGATAAGAAGAGA | 355 |
| Staphylococcus aureus USA300 | SNP | USA300_UT1 | GCACGTTGATGACTTCTGACA | 356 |
| | | | GCCCACAAACAATCCAACCTTAC | 357 |
| S. aureus 008 (excluding 5T239) | SNP | 008_UT1 | TGCCCATAACACATTTGACACTTT | 358 |
| | | | TTCGGCCACAGCTAAACTCG | 359 |
| S. aureus USA300/500 | SNP | USA3-500_UT1 | ACCTTATACGGAACATAGCAGACG | 360 |
| | | | TCGATGCGCTTCTATCACTTC | 361 |
| S. aureus Archaic Iberian | SNP | ArchIber_UT_B+ | CGCCAAATGACTCGCATTGT | 362 |
| | | | GCATGTGCCTTTCCGAARTAAA | 363 |
| S. aureus True Iberian | SNP | TruIber_UT1 | GCGCAACAGGGAAGCAA | 364 |
| | | | TGCGGATGTCCTATGTCTGAAAG | 365 |
| S. aureus ST239 | SNP | ST239_UT1 | CATGACCGCCACTATAACCAGA | 366 |
| | | | ATGCAACATTAGCAGGAGGATG | 367 |
| S. aureus CC5 | SNP | CC5_UT1 | CTGGCGCTCTCCAGCA | 368 |
| | | | TTGCAATTAGTGTGTTAGGTGGTAA | 369 |
| E. coli strain ID | E. coli H30-Rx | H30-Rx-snp200_UT | GACACCATGCGTTTTGCTTC | 370 |
| | | | TCGTACCGGCAACAATTGAC | 371 |
| | E. coli H30-Rx | H30-Rx-snp264_UT | GTGGCGATTTCACGCTGTTA | 372 |
| | | | TATCCAGCACGTTCCAGGTG | 373 |
| | trpA | trpA_ST131_016_UT | AAAACCGCGCCGCGTTACCT | 374 |
| | | | CCAGAAATCGCGCCCCGCATT | 375 |
| | pabB | pabB_ST131_025b | TCCAGCAGGTGCTGGATCGT | 376 |
| | | | GCGAAATTTTCGCCGTACTGT | 377 |
| | uidA | uidA_1_UT | CATTACGGCAAAGTGTGGGTCAAT | 378 |
| | | | CCATCAGCACGTTATCGAATCCTT | 379 |
| | uidA | uidA_2_UT | CGTATCACHGTTTGTGTGAACAA | 380 |
| | | | GGATTCACYACTTGCAAAGTCC | 381 |
| | rfb016 | rfb016_UT | ATACCGACGACGCCGATCTG | 382 |
| | | | GGATCATTTATGCTGGTACG | 383 |
| | rfb025b | rfb025b_UT | ATACCGACGACGCCGATCTG | 384 |
| | | | TGCTATTCATTATGCGCAGC | 385 |
| K. pneumo MLST | rpoB gene | KpST-rpoB_UT | GGCGAAATGGCWGAGAACCA | 386 |
| | | | GAGTCTTCGAAGTTGTAACC | 387 |
| | gapA | KpST-gapA_UT | TGAAATATGACTCCACTCACGG | 388 |
| | | | CTTCAGAAGCGGCTTTGATGGCTT | 389 |
| | mdh | KpST-mdh_UT | CCCAACTCGCTTCAGGTTCAG | 390 |
| | | | CCGTTTTCCCCAGCAGCAG | 391 |
| | phosphoglucose isomerase | KpST-pgi_UT | GAGAAAAACCTGCCTGTACTGCTGGC | 392 |
| | | | CGCGCCACGCTTTATAGCGGTTAAT | 393 |
| | phoE | KpST-phoE_UT | ACCTACCGCAACACCGACTTCTTCGG | 394 |
| | | | TGATCAGAACTGGTAGGTGAT | 395 |
| | infB | KpST-infB_UT | CTCGCTGCTGGACTATATTCG | 396 |
| | | | CGCTTTCAGCTCAAGAACTTC | 397 |
| | tonB | KpST-tonB_UT | CTTTATACCTCGGTACATCAGGTT | 398 |
| | | | ATTCGCCGGCTGRGCRGAGAG | 399 |

TABLE 9 -continued

Oligonucleotides of Lineage Identification Assays

| Target purpose | Target ID | Assay | Sequence | SEQ ID NO: |
|---|---|---|---|---|
| ST258 ID assay/ Kp-species ID | SNP 3576137-Y | ST258_UT_FB | ATGGTGGTGCGCCAGTG | 400 |
| | | | GCTGACCGAGACGTTGTC | 401 |
| CG258 ID assay | | CG258_UT_FB | ACGGCAGGCGATTTGATTTAACG | 402 |
| | | | AGCTGCGTGATCGAGACCTATC | 403 |
| E. coli MLST | adk | EcST-adk_UT | TCATCATCTGCACTTTCCGC | 404 |
| | | | CCAGATCAGCGCGAACTTCA | 405 |
| | fumC | EcST-fumC_UT | TCACAGGTCGCCAGCGCTTC | 406 |
| | | | TCCCGGCAGATAAGCTGTGG | 407 |
| | gyrB | EcST-gyrB_UT | TCGGCGACACGGATGACGGC | 408 |
| | | | GTCCATGTAGGCGTTCAGGG | 409 |
| | icd | EcST-icd_UT | ATGGAAAGTAAAGTAGTTGTTCCGGCACA | 410 |
| | | | GGACGCAGCAGGATCTGTT | 411 |
| | mdh | EcST-mdh_UT | AGCGCGTTCTGTTCAAATGC | 412 |
| | | | CAGGTTCAGAACTCTCTCTGT | 413 |
| | purA | EcST-purA_UT | TCGGTAACGGTGTTGTGCTG | 414 |
| | | | CATACGGTAAGCCACGCAGA | 415 |
| | recA | EcST-recA_UT | ACCTTTGTAGCTGTACCACG | 416 |
| | | | AGCGTGAAGGTAAAACCTGTG | 417 |
| S. aureus MLST | arc | SaST-arc_UT | TTGATTCACCAGCGCGTATTGTC | 418 |
| | | | AGGTATCTGCTTCAATCAGCG | 419 |
| | aro | SaST-aro_UT | ATCGGAAATCCTATTTCACATTC | 420 |
| | | | GGTGTTGTATTAATAACGATATC | 421 |
| | gip | SaST-glp_UT | CTAGGAACTGCAATCTTAATCC | 422 |
| | | | TGGTAAAATCGCATGTCCAATTC | 423 |
| | gmk | SaST-gmk_UT | ATCGTTTTATCGGGACCATC | 424 |
| | | | TCATTAACTACAACGTAATCGTA | 425 |
| | pta | SaST-pta_UT | GTTAAAATCGTATTACCTGAAGG | 426 |
| | | | GACCCTTTTGTTGAAAAGCTTAA | 427 |
| | tpi | SaST-tpi_UT | TCGTTCATTCTGAACGTCGTGAA | 428 |
| | | | TTTGCACCTTCTAACAATTGTAC | 429 |
| | yqi | SaST-yqi_UT | CAGCATACAGGACACCTATTGGC | 430 |
| | | | CGTTGAGGAATCGATACTGGAAC | 431 |

What is claimed is:

1. A method of detecting and characterizing one or more microorganisms within a sample, the method comprising the steps of:
receiving the sample;
extracting a template from the sample;
performing a multiplex polymerase chain reaction assay comprising the steps of:
amplifying a first marker from the template to create a first amplicon, comprising mixing the template with a first oligonucleotide comprising a sequence selected from SEQ ID Nos: 1-49, 54-109 and a first universal tail sequence; and a second oligonucleotide comprising a sequence selected from SEQ ID Nos: 1-49, 54-109 and a second universal tail sequence, wherein the first oligonucleotide and the second oligonucleotide independently comprise sequences selected from SEQ ID Nos: 1-49, 54-109 and wherein the first marker is specific for at least a genus of microorganism;
amplifying a second marker from the template to create a second amplicon, comprising mixing the template with a third oligonucleotide comprising a first universal tail sequence and a fourth oligonucleotide comprising a second universal tail sequence, wherein the second marker is specific for at least one antibiotic resistance gene;
amplifying a third marker from the template to create a third amplicon, comprising mixing the template with a fifth oligonucleotide comprising a first universal tail sequence and a sixth oligonucleotide comprising a second universal tail, wherein the third marker is specific for strain identity and/or lineage of the one or more microorganisms;
wherein the multiplex polymerase chain reaction assay is performed within a single reaction vessel; and
sequencing the first, second, and third amplicons to detect and characterize the one or more microorganisms.

2. The method of claim 1, wherein the third and fourth oligonucleotide independently comprise a sequence selected from SEQ ID NOs: 110-298.

3. The method of claim 1, wherein the fifth and sixth oligonucleotide independently comprise a sequence selected from SEQ ID NOs: 299-431.

4. The method of claim 1, further comprising adding an index to the first amplicon, second amplicon, and third amplicon using at least one indexing oligonucleotide, wherein the at least one indexing oligonucleotide comprises a complementary sequence that recognizes at least one of the first universal tail sequence and the second universal tail sequence.

5. The method of claim 1, wherein at least one of the one or more microorganisms is a pathogenic microorganism selected from the group consisting of *Enterococcus faecium, Staphylococcus aureus, Klebsiella pneumoniae, Acinetobacter baumannii, Pseudomonas aeruginosa*, and *Enterobacter* spp.

6. The method of claim 1, wherein the template comprises nucleic acids from a subject and the one or more microorganisms and the template comprises DNA.

7. The method of claim 1, wherein the subject is an animal.

8. The method of claim 7, wherein the animal is a human.

9. The method of claim 1, wherein the sample is selected from at least one of a respiratory sample, a nasal swab sample, a urine sample, and a blood sample.

10. A method of detecting and characterizing one or more microorganisms within a sample, the method comprising the steps of:
receiving the sample;
extracting a template from the sample;
performing a multiplex polymerase chain reaction assay comprising the steps of:
amplifying a first marker from the template to create a first amplicon, comprising mixing the template with a first oligonucleotide comprising a sequence selected from SEQ ID Nos: 54-57 and a first universal tail sequence; and a second oligonucleotide comprising a sequence selected from SEQ ID Nos: 54-57 and a second universal tail sequence, wherein the first oligonucleotide and the second oligonucleotide independently comprise sequences selected from SEQ ID Nos: 54-57 and wherein the first marker is specific for at least a genus of microorganism;
amplifying a second marker from the template to create a second amplicon, comprising mixing the template with a third oligonucleotide comprising a first universal tail sequence and a fourth oligonucleotide comprising a second universal tail sequence, wherein the second marker is specific for at least one antibiotic resistance gene;
amplifying a third marker from the template to create a third amplicon, comprising mixing the template with a fifth oligonucleotide comprising a first universal tail sequence and a sixth oligonucleotide comprising a second universal tail, wherein the third marker is specific for strain identity and/or lineage of the one or more microorganisms;
wherein the multiplex polymerase chain reaction assay is performed within a single reaction vessel; and
sequencing the first, second, and third amplicons to detect and characterize the one or more microorganisms.

11. The method of claim 10, wherein the third and fourth oligonucleotide independently comprise a sequence selected from SEQ ID NOs: 110-298.

12. The method of claim 10, wherein the fifth and sixth oligonucleotides independently comprise a sequence selected from SEQ ID NOs:299-431.

13. The method of claim 10, further comprising adding an index to the first amplicon, second amplicon, and third amplicon using at least one indexing oligonucleotide, wherein the at least one indexing oligonucleotide comprises a complementary sequence that recognizes at least one of the first universal tail sequence and the second universal tail sequence.

14. The method of claim 10, wherein the template comprises nucleic acids from a subject and the one or more microorganisms and the template comprises DNA.

15. The method of claim 10, wherein the subject is an animal.

16. The method of claim 15, wherein the animal is a human.

17. The method of claim 10, wherein the sample is selected from at least one of a respiratory sample, a nasal swab sample, a urine sample, and a blood sample.

* * * * *